United States Patent
Vendrely et al.

(10) Patent No.: US 6,655,828 B2
(45) Date of Patent: Dec. 2, 2003

(54) BONE CEMENT MIXING APPARATUS HAVING IMPROVED MIXING BLADE CONFIGURATION

(75) Inventors: Timothy G. Vendrely, Warsaw, IN (US); Sam Sackett, Ft. Wayne, IN (US)

(73) Assignee: DePuy Orthopaedics, Inc., Warsaw, IN (US)

( * ) Notice: Subject to any disclaimer, the term of this patent is extended or adjusted under 35 U.S.C. 154(b) by 92 days.

(21) Appl. No.: 10/002,729

(22) Filed: Nov. 15, 2001

(65) Prior Publication Data

US 2002/0067658 A1 Jun. 6, 2002

Related U.S. Application Data

(60) Provisional application No. 60/250,808, filed on Dec. 1, 2000.

(51) Int. Cl.[7] .............................. B01F 7/20; B01F 13/06; B01F 15/02
(52) U.S. Cl. ..................... 366/139; 366/169.2; 366/243
(58) Field of Search .............................. 366/139, 169.2, 366/243, 169.1, 189

(56) References Cited

U.S. PATENT DOCUMENTS

| | | | |
|---|---|---|---|
| 215,850 A | 5/1879 | Whelchel | |
| 341,306 A | 5/1886 | Allen | |
| 347,916 A | 8/1886 | Bogart | |
| 409,533 A | 8/1889 | Walter | |
| 642,650 A | 2/1900 | Walker et al. | |
| 2,696,022 A | 12/1954 | Steinbock et al. | |
| 3,067,988 A | * 12/1962 | Rodoz | 366/265 |
| 3,144,966 A | * 8/1964 | Cook | 222/136 |
| 4,185,072 A | 1/1980 | Puderbaugh et al. | 366/139 |
| 4,297,214 A | * 10/1981 | Guarnaschelli | 210/219 |
| 4,638,676 A | * 1/1987 | Lively et al. | 74/31 |
| 4,889,432 A | * 12/1989 | Patterson | 366/139 |
| 4,961,647 A | 10/1990 | Coutts et al. | 366/139 |
| 5,015,101 A | * 5/1991 | Draenert | 366/130 |
| 5,252,301 A | * 10/1993 | Nilson et al. | 366/139 |
| 5,368,386 A | 11/1994 | Murray | 366/139 |
| 5,415,474 A | 5/1995 | Nelson et al. | 366/139 |
| 5,494,349 A | 2/1996 | Seddon | 366/139 |
| 5,549,381 A | 8/1996 | Hays et al. | 366/139 |
| 5,551,778 A | 9/1996 | Hauke et al. | 366/139 |
| 5,588,745 A | * 12/1996 | Tanaka et al. | 366/130 |
| 5,797,678 A | 8/1998 | Murray | 366/139 |
| 5,797,679 A | 8/1998 | Grulke et al. | 366/139 |
| 5,842,785 A | 12/1998 | Brown et al. | 366/139 |
| 5,842,786 A | 12/1998 | Solomon | 366/139 |
| 5,857,771 A | 1/1999 | Draenert | 366/130 |
| 5,924,324 A | * 7/1999 | Kilker et al. | 74/89.18 |
| 5,934,803 A | * 8/1999 | Hutter | 366/139 |
| 5,975,751 A | 11/1999 | Earle | 366/139 |
| 6,017,349 A | * 1/2000 | Heller et al. | 366/139 |
| 6,024,480 A | 2/2000 | Seaton et al. | 366/130 |
| 6,033,105 A | 3/2000 | Barker et al. | 366/189 |
| 6,042,262 A | 3/2000 | Hajianpour | 366/139 |
| 6,116,773 A | * 9/2000 | Murray | 366/139 |
| 6,120,174 A | * 9/2000 | Hoag et al. | 366/139 |
| 6,491,423 B1 | 12/2002 | Skibo et al. | 366/146 |

FOREIGN PATENT DOCUMENTS

| | | |
|---|---|---|
| FR | 711436 | 5/1930 |
| GB | 590559 | 7/1947 |
| WO | WO 95/13862 | 5/1995 |

* cited by examiner

Primary Examiner—Tony G. Soohoo
(74) Attorney, Agent, or Firm—Maginot, Moore & Beck

(57) ABSTRACT

A bone cement mixing device has a canister which is modular in design and constructed from a transparent material. The mixing device further has a mixing head assembly having a crank that is operatively coupled to a mixing blade via a gear train. The gear train is configured to drive the mixing blade in a reciprocating manner including the varying of the angular velocity, direction of travel, and angular distance of travel of the blade while the crank is rotated at a constant velocity and direction. The mixing blade has a fluid passage defined therein which allows the liquid cement component to be delivered at various locations within the mixing chamber of the canister. A method of mixing bone cement is also disclosed.

25 Claims, 20 Drawing Sheets

BONE CEMENT MIXING APPARATUS HAVING IMPROVED MIXING BLADE CONFIGURATION

PROVISIONAL PATENT APPLICATION

This application claims the benefit of U.S. Provisional Application Ser. No. 60/250,808, filed Dec. 1, 2000. The disclosure of the above-identified provisional patent application is hereby totally incorporated by reference in its entirety.

CROSS REFERENCE

Cross reference is made to copending U.S. utility patent application Ser. No. 10/002045, entitled "Bone Cement Mixing Apparatus having Improved Gearing Arrangement for Driving a Mixing Blade" by Timothy G. Vendrely, Jack F. Long, Christopher Battles, Paul DeCesare, Patrick Gutelius, and Sam Sackett which is assigned to the same assignee as the present invention and which is filed concurrently herewith. The disclosure of the above-identified utility patent application is hereby totally incorporated by reference in its entirety.

TECHNICAL FIELD OF THE INVENTION

The present invention relates generally to a surgical assembly, and more particularly to an apparatus and method for mixing bone cement.

BACKGROUND OF THE INVENTION

It is necessary in many orthopedic surgical procedures to employ a cement or grouting type agent, such as for attaching artificial joint implants, repairing or forming joints in bones, or other forms of orthopedic work. The type of cement generally used for these purposes is a self-curing resin formed from the blending of a wide variety of liquid monomers or comonomers with powdered polymers or copolymers to form a viscous admixture to be used as the grouting agent.

The admixture of the powder and liquid components develops a quick setting material. As such, preparation of the cement usually occurs directly within the operating area just prior to use. In particular, a bone cement mixing apparatus is generally utilized to mix the powder and liquid components in the operating area. The resultant admixture is then removed from the mixing apparatus and placed in a cement delivery apparatus for subsequent use by the surgeon. Specifically, the bone cement must generally first be scooped or otherwise removed from the mixing apparatus and thereafter placed in a syringe-type delivery apparatus for use by the surgeon.

The aforedescribed system for mixing and delivering bone cement has a number of drawbacks associated therewith. For example, monomer vapors are generated during the depositing of the monomer into the mixing apparatus and during the subsequent mixing of the monomer with the powder component of the bone cement. Such monomer vapors may be noxious and/or toxic. Because the bone cement is generally mixed in the operating room environment, it is important to prevent any monomer or its vapors from escaping the mixing apparatus. However, heretofore designed mixing apparatus have not included mechanisms for controlling the escape of such vapors.

Moreover, heretofore designed mixing apparatus have been plagued with problems relating to the incomplete mixing of the liquid component and the powder component. Specifically, the powder component and liquid component are often inadequately mixed during operation of heretofore designed systems. Such a problem is further compounded by the fact that heretofore designed mixing vessels are not transparent thereby preventing the contents of the vessel (i.e. the bone cement) from being viewed by the operator of the mixing apparatus.

In addition, the aforedescribed system also suffers from operational inefficiencies relating to the need to transfer the mixed bone cement from the mixing apparatus to the delivery apparatus. Specifically, the need to remove the mixed bone cement from one device (i.e. the mixing apparatus) and place it in a second device (i.e. the delivery device) creates an extra step in the process thereby increasing the time necessary to deliver the mixed bone cement. Moreover, a quantity of the bone cement is lost in the process since it is highly unlikely that all of the mixed cement is actually removed from the mixing apparatus and placed in the delivery apparatus.

What is needed therefore is an apparatus and method for mixing a bone cement which overcomes one or more of the above-mentioned drawbacks. What is particularly needed is an apparatus and method for mixing bone cement which reduces, if not eliminates, exposure to vapors from the liquid bone cement component within the operating area. What is further needed is an apparatus and method for mixing bone cement which may also be utilized to delivery the mixed bone cement. What is moreover needed is an apparatus and method for mixing bone cement which reduces, or even eliminates, the occasions in which a portion of the powder cement component is not thoroughly mixed with the liquid cement component.

SUMMARY OF THE INVENTION

In accordance with the concepts of the present invention, there is provided a bone cement mixing apparatus. The bone cement mixing apparatus includes a handle, and a canister defining a mixing chamber. The bone cement mixing apparatus further includes a mixing blade which is caused to rotate in response to movement of the handle, the mixing blade being positioned within the mixing chamber. The mixing blade includes a shaft and at least one vane supported by the shaft. Also, the shaft has defined therein (i) an inlet orifice, (ii) a plurality of outlet orifices, and (iii) a passageway which places the inlet orifice in fluid communication with each of the plurality of outlet orifices.

Pursuant to another embodiment of the present invention, there is provided a method of mixing bone cement. The method includes the step of (i) placing a powder bone cement component within a canister, (ii) sealing the canister after the placing step, (iii) advancing a liquid bone cement component through a mixing blade located within the canister after the sealing step, and (iv) rotating the mixing blade after the liquid bone cement component is advanced through the mixing blade. The mixing blade includes (i) an inlet orifice, (ii) a plurality of outlet orifices, and (iii) a passageway which places the inlet orifice in fluid communication with each of the plurality of outlet orifices. In addition, the advancing step includes the step of advancing the liquid bone cement component (i) into the mixing blade through the inlet orifice, (ii) through the passageway, and (iii) out of the mixing blade through the plurality of outlet orifices.

Yet according to another embodiment of the present invention, there is provided a bone cement mixing apparatus. The bone cement mixing apparatus includes a container defining a mixing chamber. Further, the bone cement mixing apparatus includes a mixing blade positioned within the mixing chamber, the mixing blade defining (i) an inlet orifice, (ii) a plurality of outlet orifices, and (iii) a passageway which places the inlet orifice in fluid communication with each of the plurality of outlet orifices.

Yet according to another embodiment of the present invention, there is provided a bone cement mixing apparatus which includes a handle. The bone cement mixing apparatus further includes a first canister segment defining a first mixing chamber portion, and a second canister segment defining a second mixing chamber portion. Also, the bone cement mixing apparatus includes a mixing blade which is caused to rotate in response to movement of the handle. The mixing blade is located within both the first mixing chamber portion and the second mixing chamber portion. Moreover, the first canister segment includes a first coupling, and the second canister segment includes a second coupling. The first coupling cooperates with the second coupling so as to secure the first canister segment to the second canister segment.

It is therefore an object of the present invention to provide a new and useful apparatus for mixing bone cement.

It is moreover an object of the present invention to provide an improved apparatus for mixing bone cement.

It is a further object of the present invention to provide a new and useful method for mixing bone cement.

It is also an object of the present invention to provide an improved method for mixing bone cement.

It is yet another object of the present invention to provide an apparatus and method for mixing bone cement which reduces, if not eliminates, exposure to vapors from the liquid bone cement component within the operating area.

It is moreover an object of the present invention to provide an apparatus and method for mixing bone cement which may also be utilized to delivery the mixed bone cement.

It is a further object of the present invention to provide an apparatus and method for mixing bone cement which reduces, or even eliminates, the occasions in which a portion of the powder cement component is not thoroughly mixed with the liquid cement component.

The above and other objects, features, and advantages of the present invention will become apparent from the following description and the attached drawings.

DETAILED DESCRIPTION OF THE INVENTION

Figure 1:
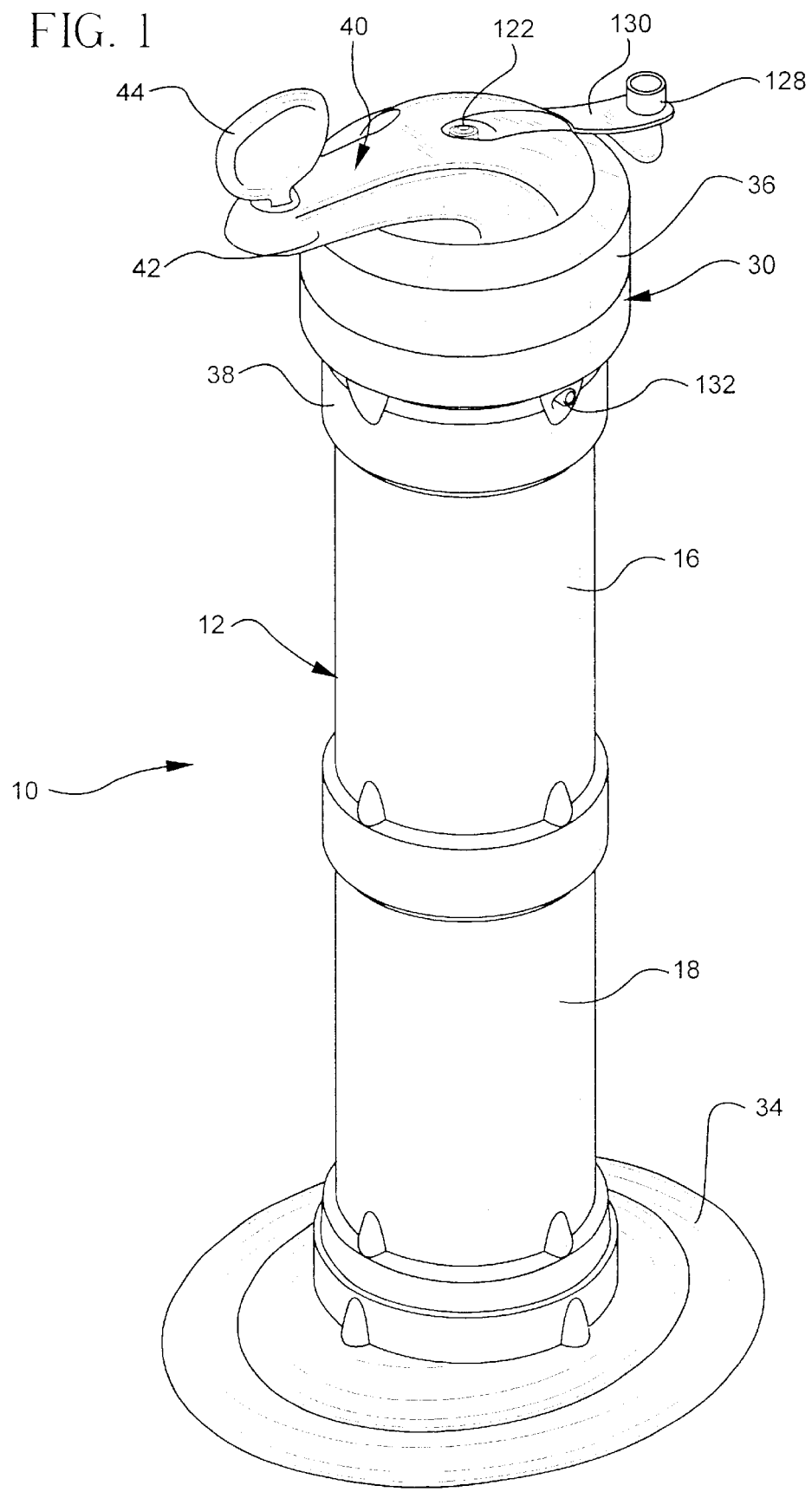
FIG. 1 is a perspective view of bone cement mixing device which incorporates the features of the present invention therein.
Figure 2:
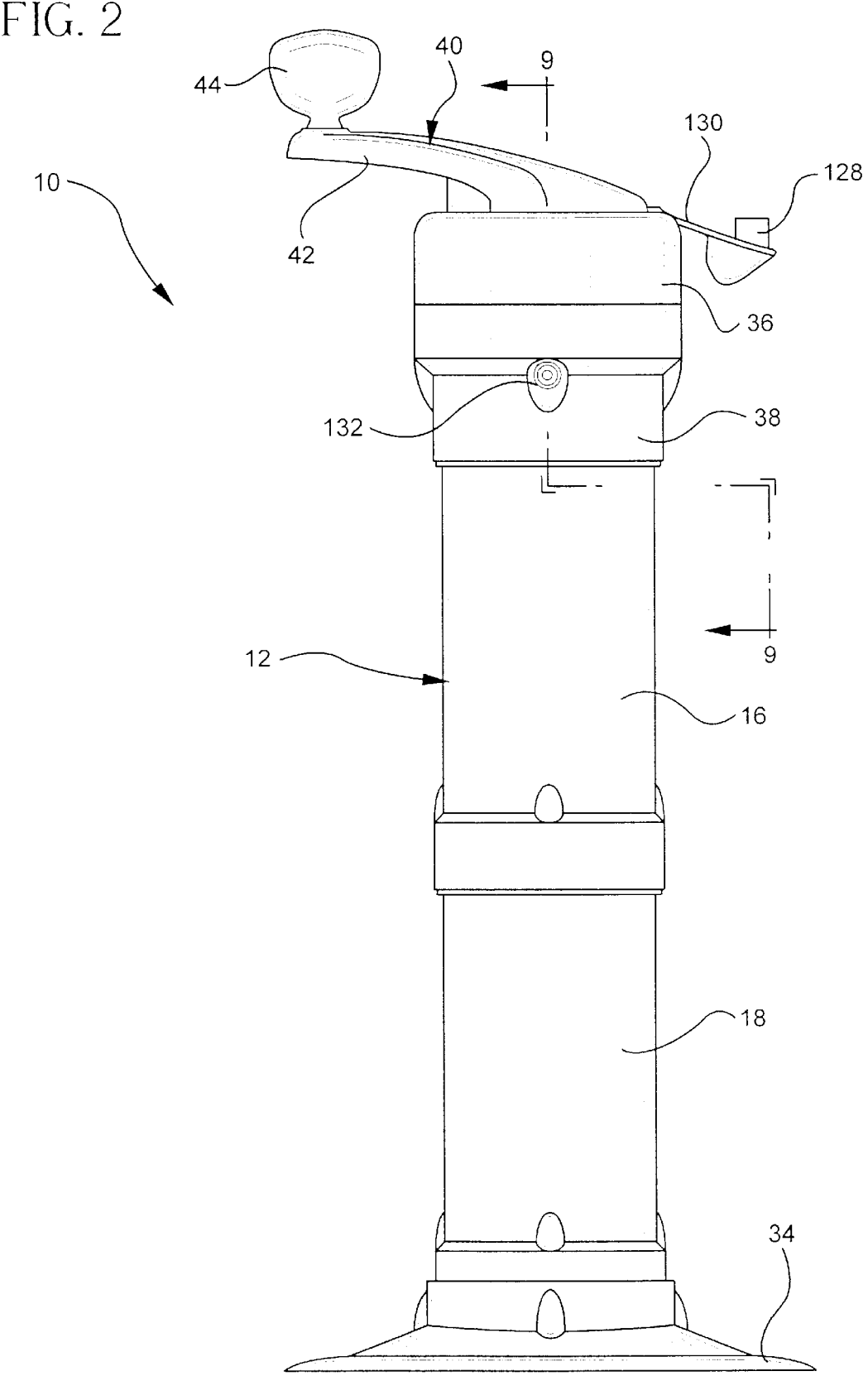
FIGS. 2–5 are side elevational views of the mixing device of FIG. 1.
Figure 3:
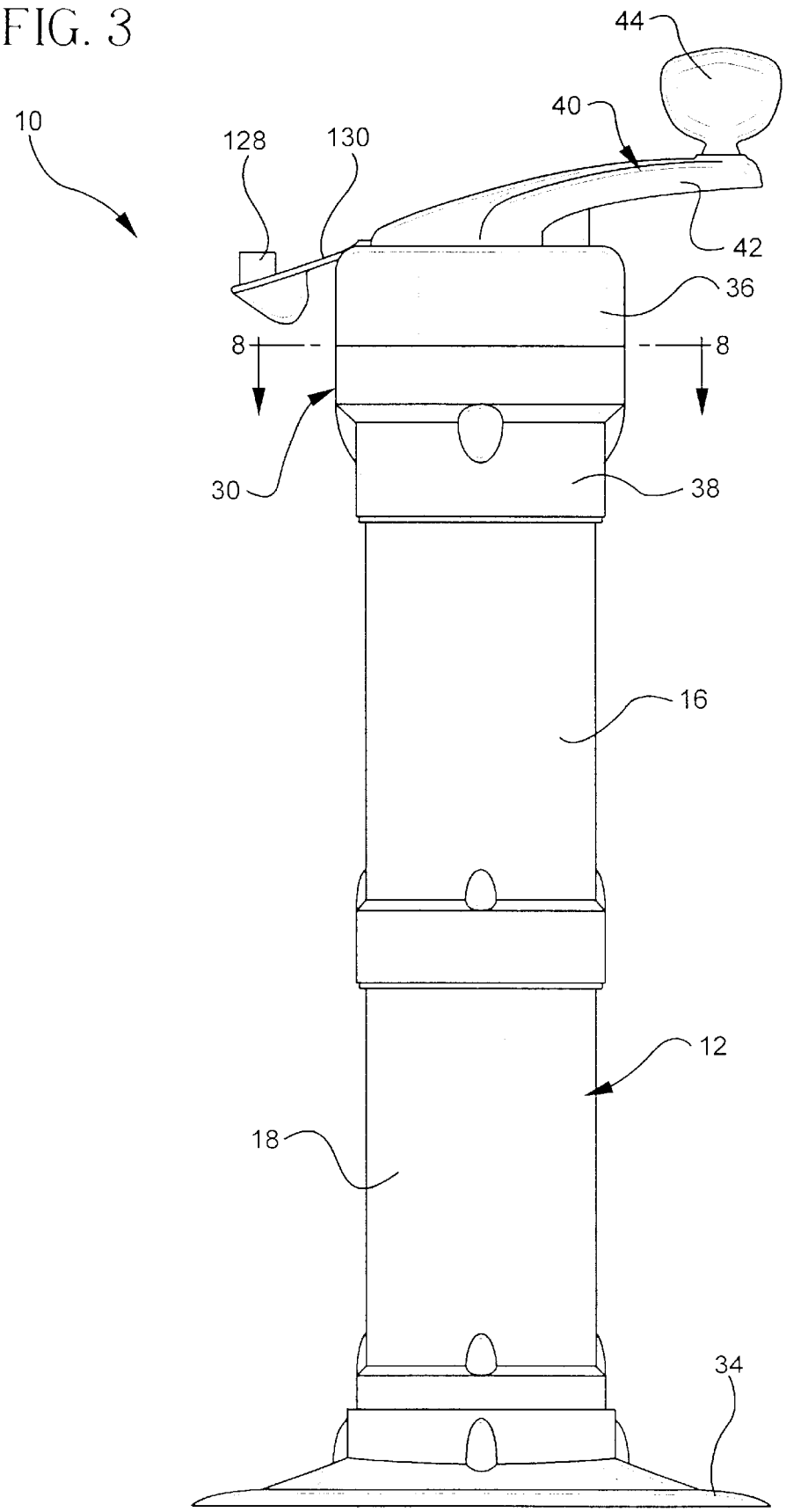
Figure 4:
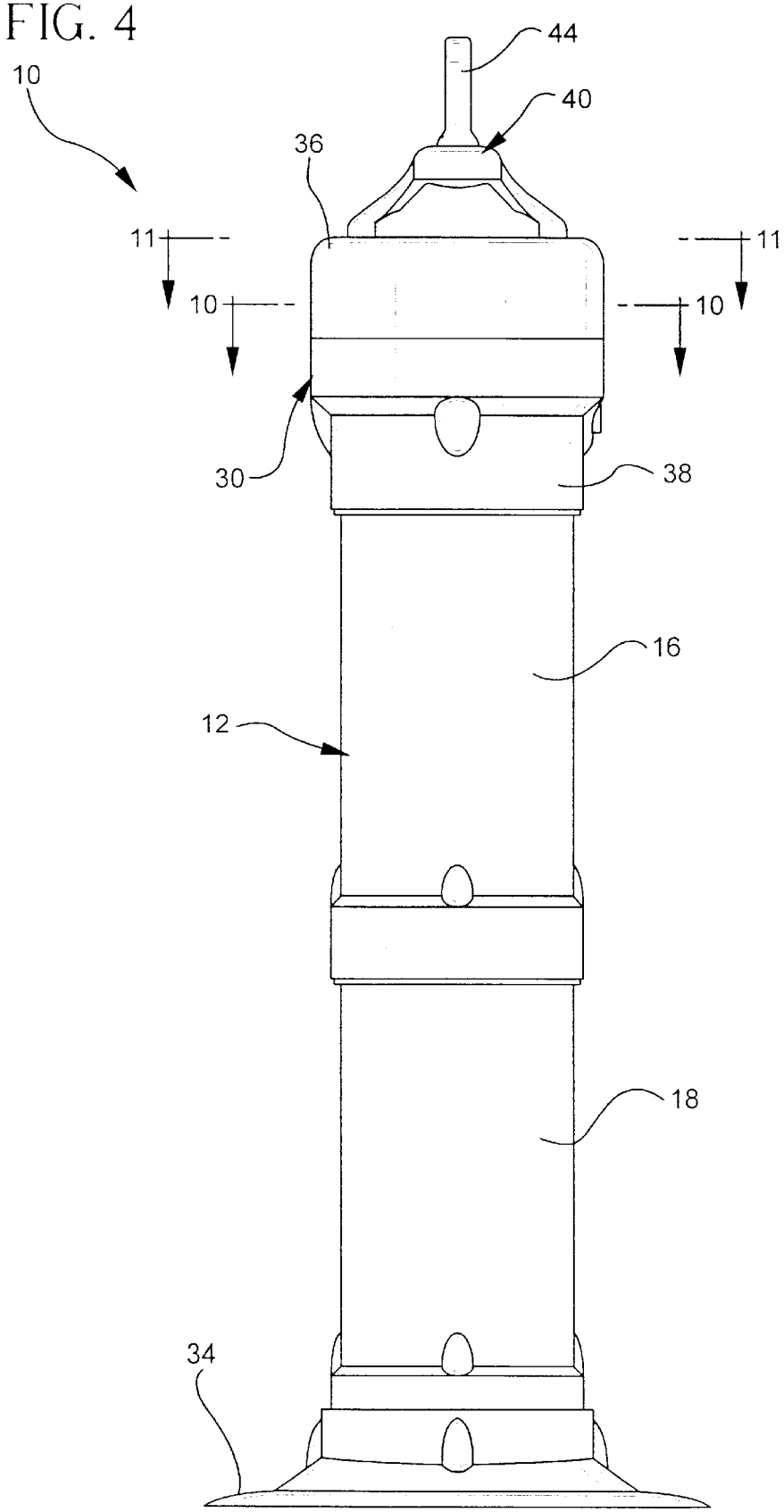
Figure 5:
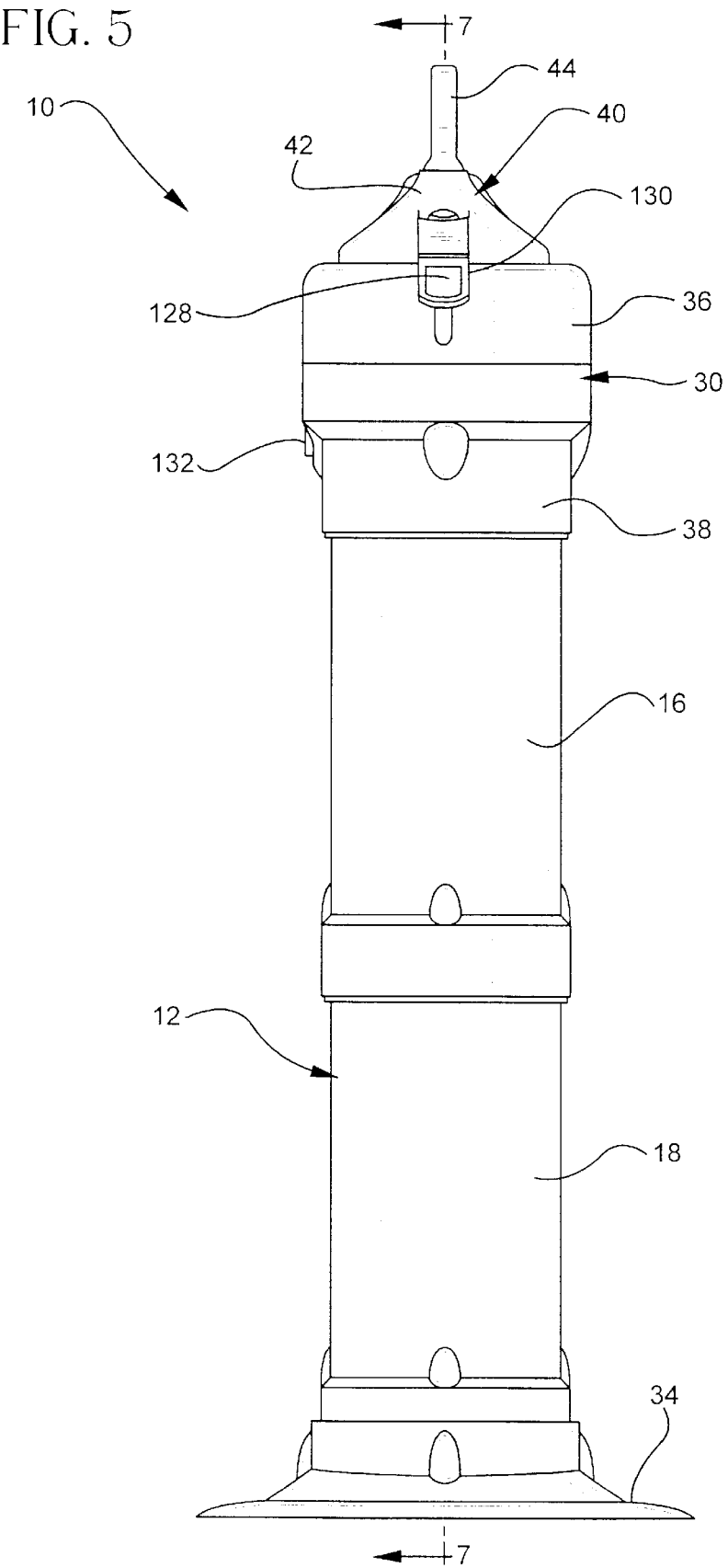
Figure 6:
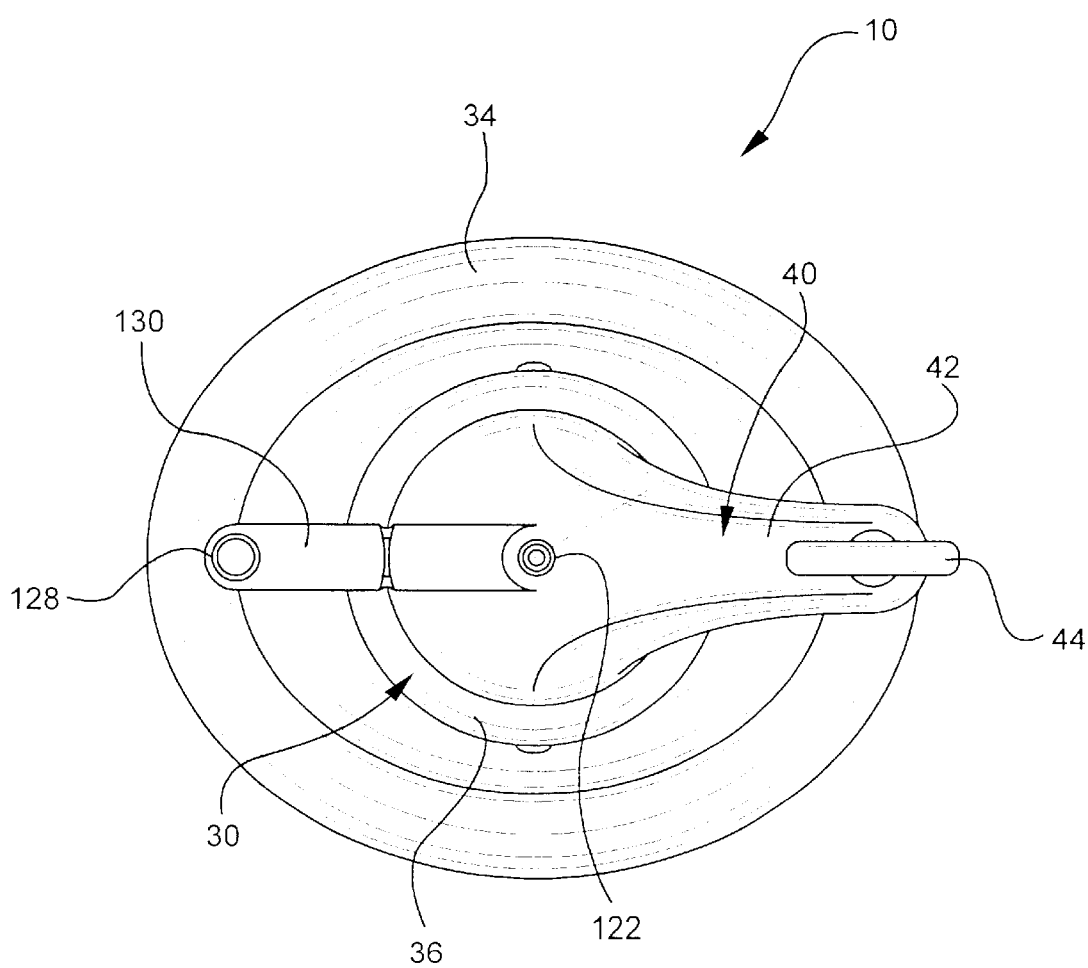
FIG. 6 is an enlarged plan view of the mixing device of FIG. 1.

While the invention is susceptible to various modifications and alternative forms, a specific embodiment thereof has been shown by way of example in the drawings and will herein be described in detail. It should be understood, however, that there is no intent to limit the invention to the particular form disclosed, but on the contrary, the intention is to cover all modifications, equivalents, and alternatives falling within the spirit and scope of the invention.

Referring now to FIGS. 1–7, there is shown a bone cement mixing device 10 which incorporates the features of the present invention therein. As shall be discussed below in greater detail, the bone cement mixing device 10 of the present invention is configured to receive a quantity of a powder bone cement component and a liquid bone cement component (e.g. a monomer) and thereafter mix the powder component and liquid component together. The bone cement mixing device 10 is also operable as a bone cement delivery device thereby eliminating the need to utilize a separate delivery device.

The mixing device 10 includes a canister 12 having a mixing chamber 14 defined therein. The canister 12 is preferably embodied as a pair of identical cylindrically-shaped cartridges 16, 18. Use of the cartridges 16, 18 allows for modular construction of the mixing device 10 while also reducing the number of different components which are utilized in the design thereof.

Each of the cartridges 16, 18 is preferably constructed of a transparent material such as a transparent plastic material. Such use of a transparent material in the construction of the cartridges 16, 18 is advantageous in that the operator the mixing device may visually observe the contents within the mixing chamber 14 (i.e. the powder and liquid cement components) in order to visually determine if the components have been adequately (i.e. thoroughly) mixed with one another.

Moreover, the cartridges 16, 18 may be constructed to accommodate any quantity of bone cement. Preferably, the cartridges 16, 18 are constructed to hold and mix at least 120 grams of powder bone cement component and the associated quantity of the liquid bone cement component (i.e. the monomer). Such a configuration is advantageous in that surgical procedures commonly require the preparation of three (3) batches of bone cement powder (with each batch being 40 grams). It is often necessary when using a heretofore designed mixing apparatus for each of the three batches to be prepared (i.e. mixed) separately thereby potentially creating delays and/or timing difficulties within the operating area during a surgical procedure. However, the mixing device 10 of the present invention overcomes this limitation by being configured to mix all three of the batches simultaneously.

Figure 7:
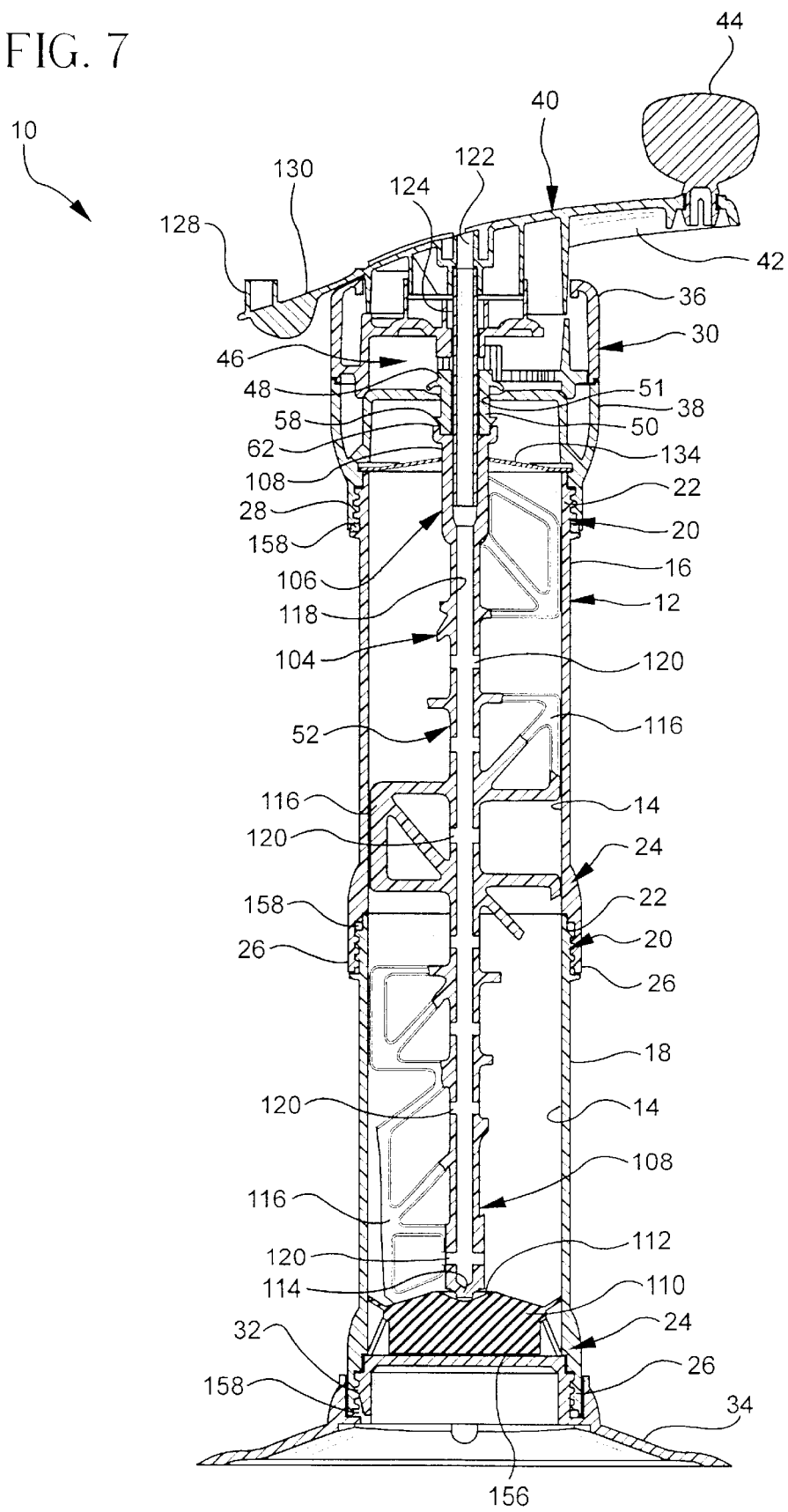
FIG. 7 is a cross sectional view of the mixing device of FIG. 1, taken along the line 7—7 of FIG. 5, as viewed in the direction of the arrows.
Figure 8:
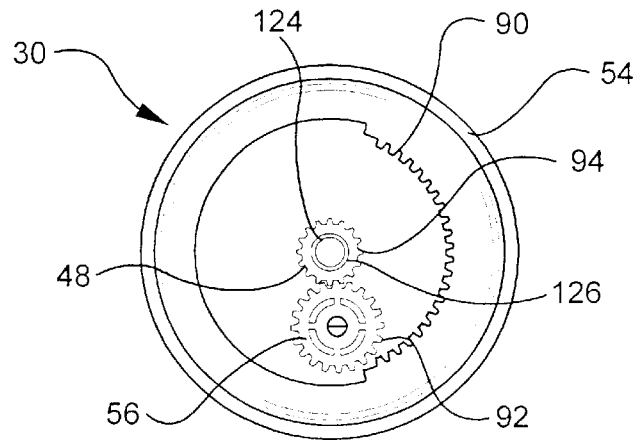
FIG. 8 is a cross sectional view taken along the line 8—8 of FIG. 3, as viewed in the direction of the arrows.

The upper end 20 of each of the cartridges 16, 18 has a first number of threads 22 defined therein, whereas the lower end 24 of each of the cartridges 16, 18 has a corresponding number of threads 26 defined therein. The threads 22, 26 may be threadingly engaged with one another (as in the case of the junction between the cartridges 16, 18), or may be engaged to a number of other components. In particular, as shown in FIG. 7, the threads 22 of the upper end 20 of the cartridge 16 are threadingly engaged with a number of threads 28 associated with a mixing head assembly 30. The threads 26 of the lower end 24 of the canister 18, on the other hand, are threadingly engaged with a number of threads 32 defined in a base 34. It should be appreciated that sealing members such as O-rings 158 (see FIGS. 7, 9, and 23) are preferably utilized at each threaded coupling (i.e. between the cartridges 16, 18, between the cartridge 16 and the mixing head assembly 30, and between the cartridge 18 and the base 34)

Figure 9:
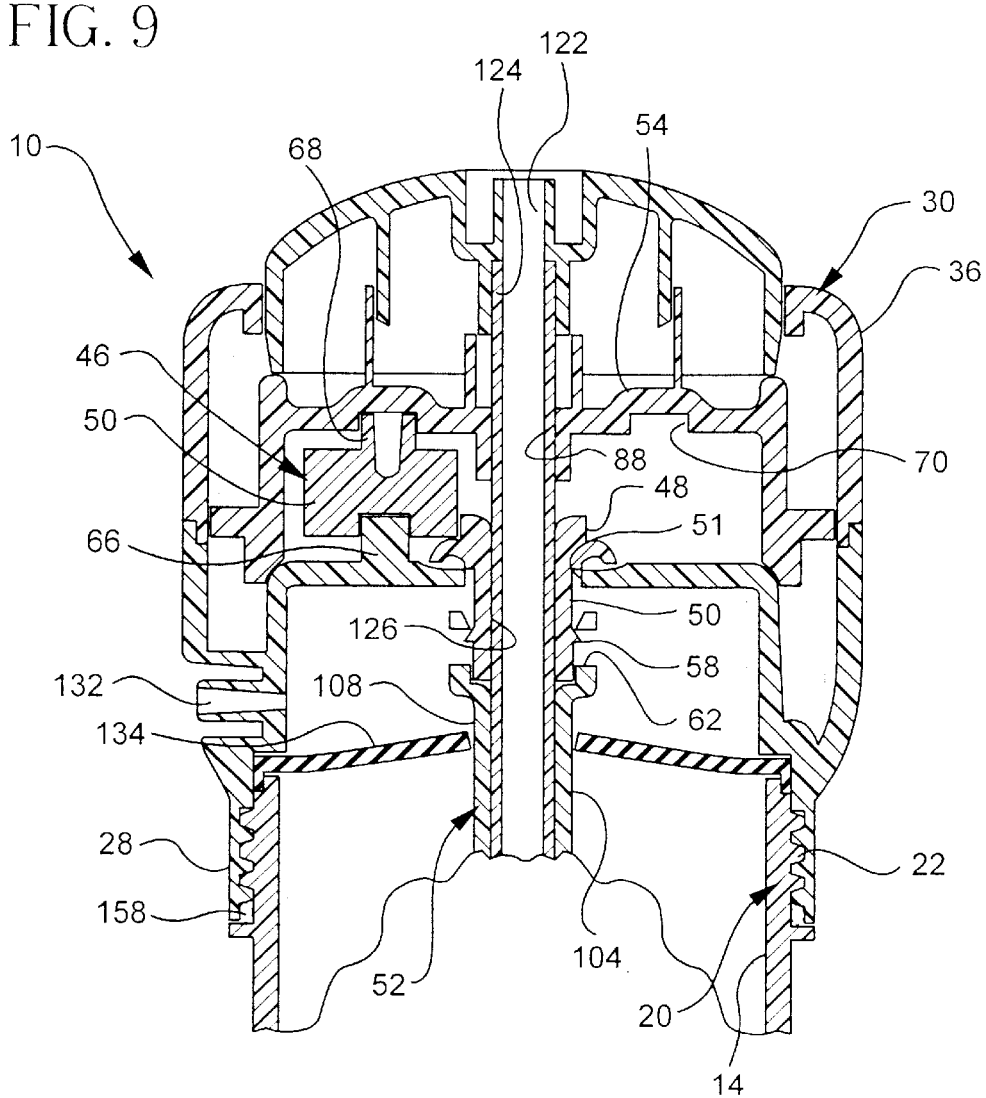
FIG. 9 is a cross sectional view taken along the line 9—9 of FIG. 2, as viewed in the direction of the arrows.
Figure 12:
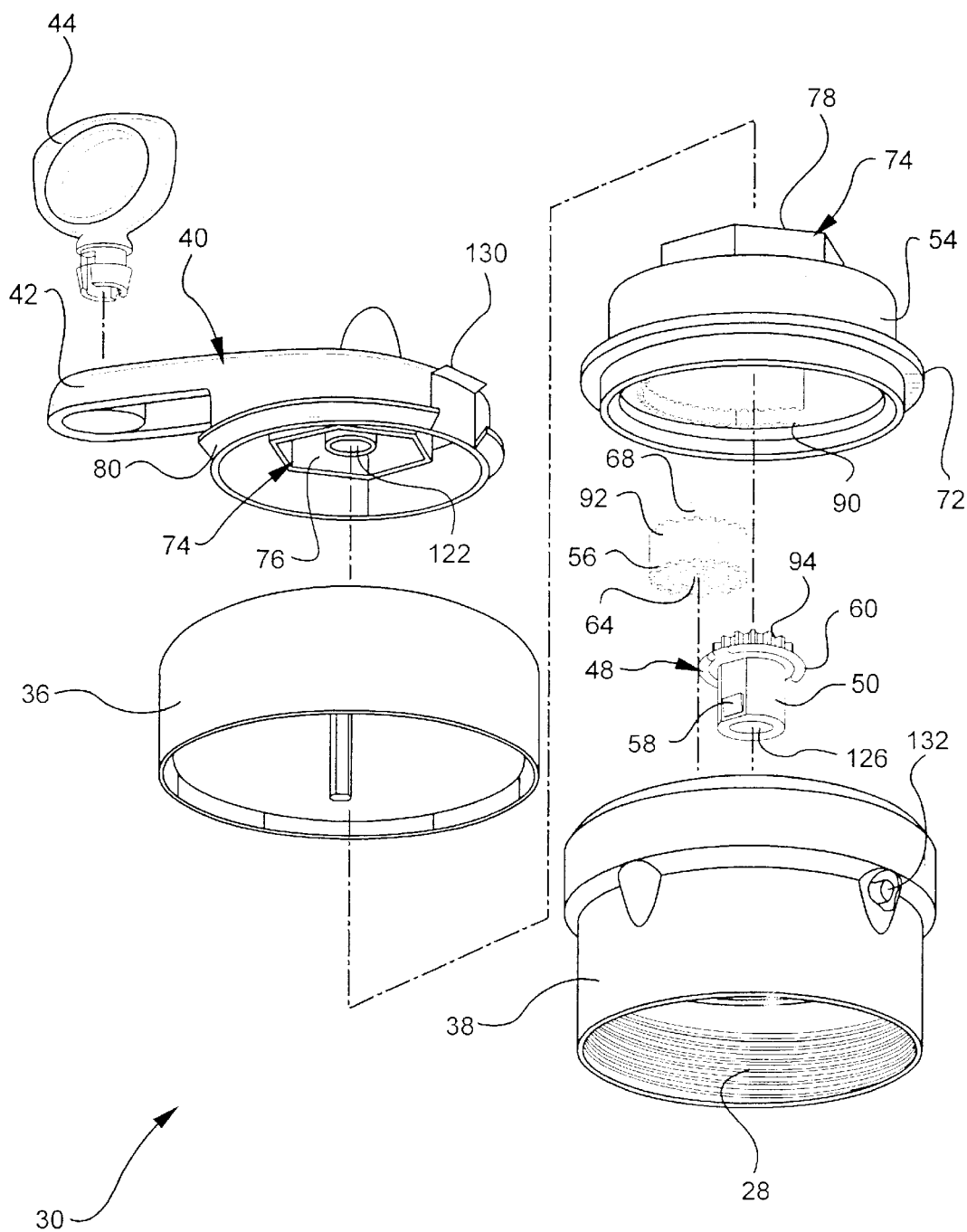
FIGS. 12–14 are exploded perspective views of the mixing head assembly of the mixing device of FIG. 1.

As shown in FIGS. 1, 7, and 9, the mixing head assembly 30 includes an upper gear housing 36 and a lower gear housing 38. The upper gear housing 36 is press fit or otherwise secured to the lower gear housing 38. The mixing head assembly 30 also includes a crank 40 which is rotatably secured to the upper gear housing 36. The crank 40 includes an elongated arm 42 having a knob 44 rotatably secured to an end thereof. As will be discussed below in greater detail, the upper gear housing 36 and the lower gear housing 38 cooperate to house a gear train 46 which is driven by rotation of the crank 40. Specifically, the gear train 46 includes an output pinion 48 which is rotatably coupled to the lower gear housing 38. The output pinion 48 includes a downwardly extending coupling portion 50 which extends through an aperture 51 defined in the lower gear housing 38 (see also FIG. 13). The coupling portion 50 of the output pinion 48 is non-rotatably secured to an upper end 106 of a mixing blade 52. In particular, as shown in FIGS. 9 and 12, the coupling portion 50 of the output pinion 48 includes a number of barbs 58 which are received into a corresponding number of slots 60 (see FIGS. 7 and 9) defined in a coupling portion 108 of the mixing blade 52. Hence, rotation of the output pinion 48 causes similar rotation (i.e. in the same direction and at the same angular velocity) of the mixing blade 52.

Figure 13:
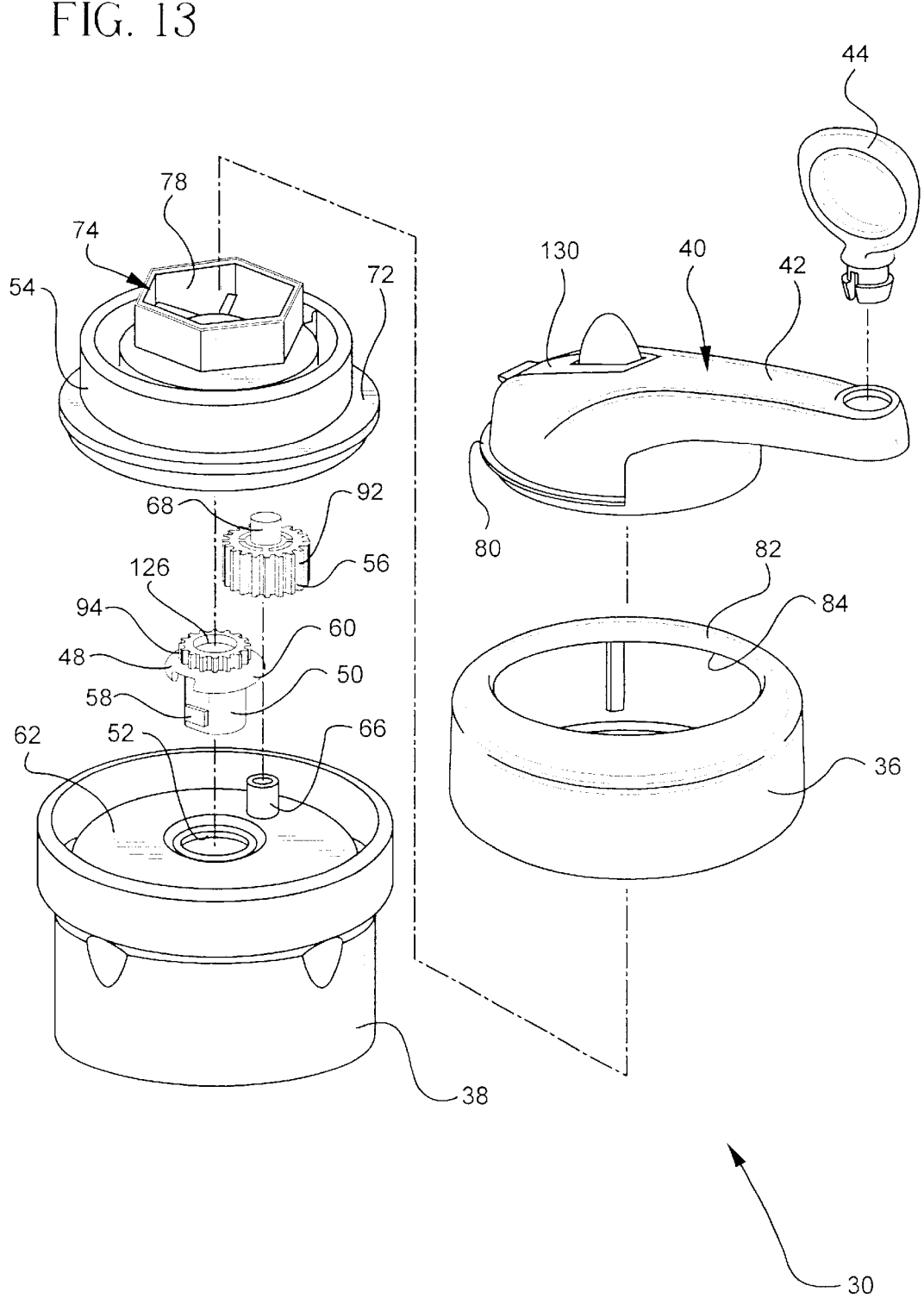
Figure 14:
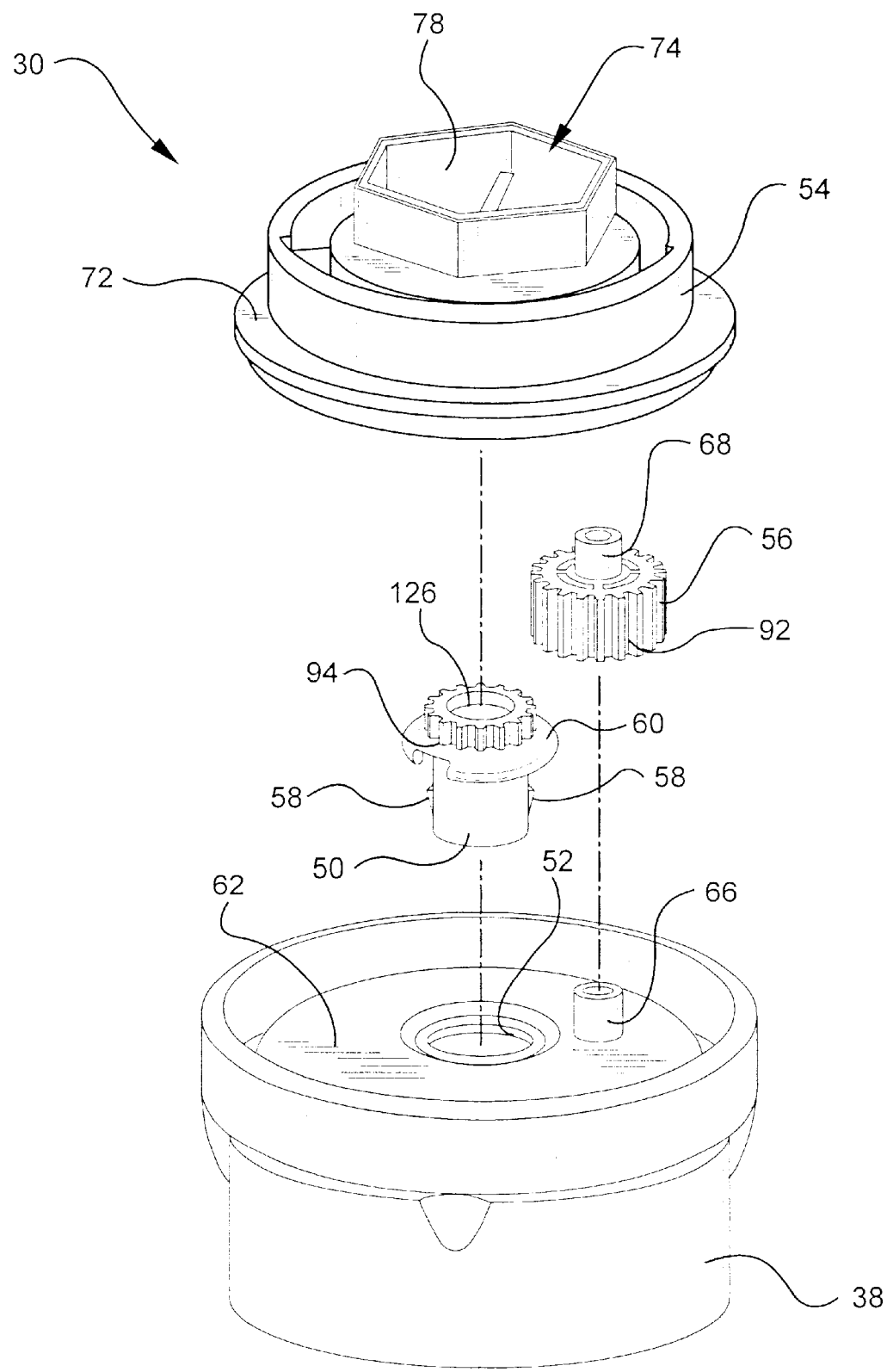

Referring now to FIGS. 12–17, the mixing head assembly 30 is shown in greater detail. In addition to the crank 40 and the gear housings 36, 38, the mixing head assembly 30 also includes a directional gear 54, an idler gear 56, and the output pinion 48. As shown in FIGS. 12 and 13, the directional gear 54, the idler gear 56, and the output pinion 48 are housed within the housing defined by the upper gear housing 36 and the lower gear housing 38. Specifically, the output pinion 48 has a shoulder 60 defined therein. Upon insertion of the coupling portion 50 of the output pinion 48 into the aperture 51 defined in the lower gear housing 38, the shoulder 60 of the output pinion 48 contacts a retaining surface 62 of the gear housing 38 (see FIG. 13) thereby retaining the output opinion 48 while also allowing it to rotate relative to the gear housing 38.

Figure 10:
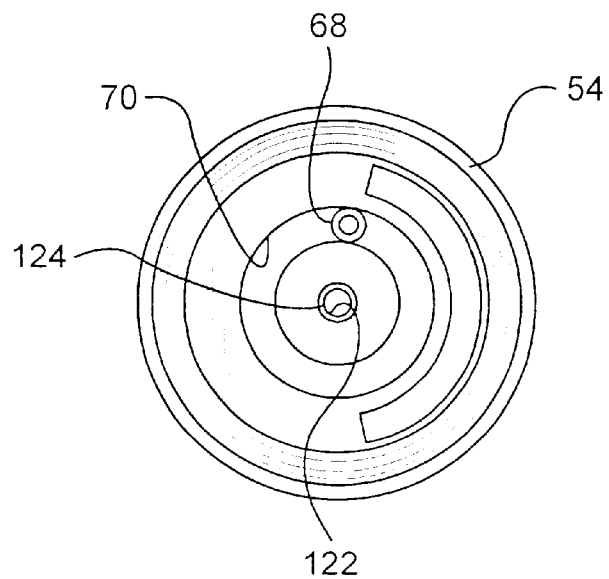
FIG. 10 is a cross sectional view taken along the line 10—10 of FIG. 4, as viewed in the direction of the arrows.

The idler gear 56 has an aperture 64 defined therein (see FIG. 12) which is received around a post 66 (see FIGS. 13 and 14) defined in the lower gear housing 38 thereby rotatably securing the idler gear 56 to the lower gear housing 38. The other end of the idler gear 56 has a post 68 extending therefrom which is received into a slot 70 defined in the body 72 of the directional gear 54 (see FIGS. 10 and 17). The post 68 is captured by or is otherwise retained within the slot 70 during rotation of the directional gear 54.

Figure 11:
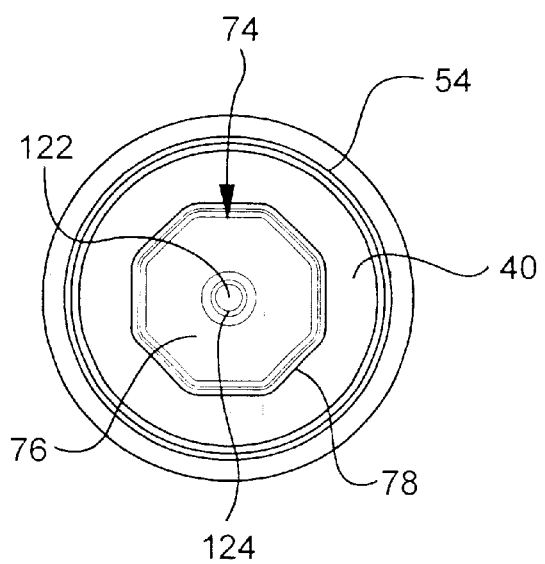
FIG. 11 is a cross sectional view taken along the line 11—11 of FIG. 4, as viewed in the direction of the arrows.

The directional gear 54 is non-rotatably secured to the crank 40 by use of a hexagonally-shaped coupling mechanism 74. In particular, the crank 40 has a hexagonally-shaped member 76 extending downwardly therefrom, whereas the body 72 of the directional gear 54 has a slightly larger hexagonally-shaped member 78 extending upwardly therefrom. During assembly of the mixing head assembly 30, a shoulder 80 of the crank is positioned in contact which a bearing surface 82 defined on the upper surface of the upper gear housing 36 (see FIG. 13) thereby allowing the hexagonally-shaped member 76 of the crank 40 to extend through a housing opening 84 defined in the upper gear housing 36. When positioned in such a manner, the hexagonally-shaped member 76 of the crank 40 may be press fit or otherwise received into the hexagonally-shaped member 78 of the directional gear 54 which is positioned within the upper gear housing 36 (see FIG. 11). When secured in such a manner, rotation of the crank 40 relative to the upper gear housing 36 causes similar rotation of the directional gear 54 relative to the upper gear housing 36. Note that the directional gear 54 is caused to rotate about a central axis CA as shown in FIG. 17.

The idler gear 56 is meshingly engaged with both the directional gear 54 and the output pinion 48. In particular, as shown in FIG. 17, the directional gear 54 includes a first number of gear teeth 86 defined in the body 72 thereof. The gear teeth 86 are positioned around a portion of the periphery of an aperture 88 which defines the axis of rotation of the directional gear 54. The directional gear 54 also includes a second number of gear teeth 90 defined in the body 72 thereof. As can be seen in FIG. 17, the gear teeth 90 are spaced radially outwardly from the gear teeth 86. As will be discussed below in greater detail, the gear teeth 86 and the gear teeth 90 selectively meshingly engage with the idler gear 56 so as to selectively drive the output pinion 48 (and hence the mixing blade 52) at varying velocities and directions of rotation.

Figure 17:
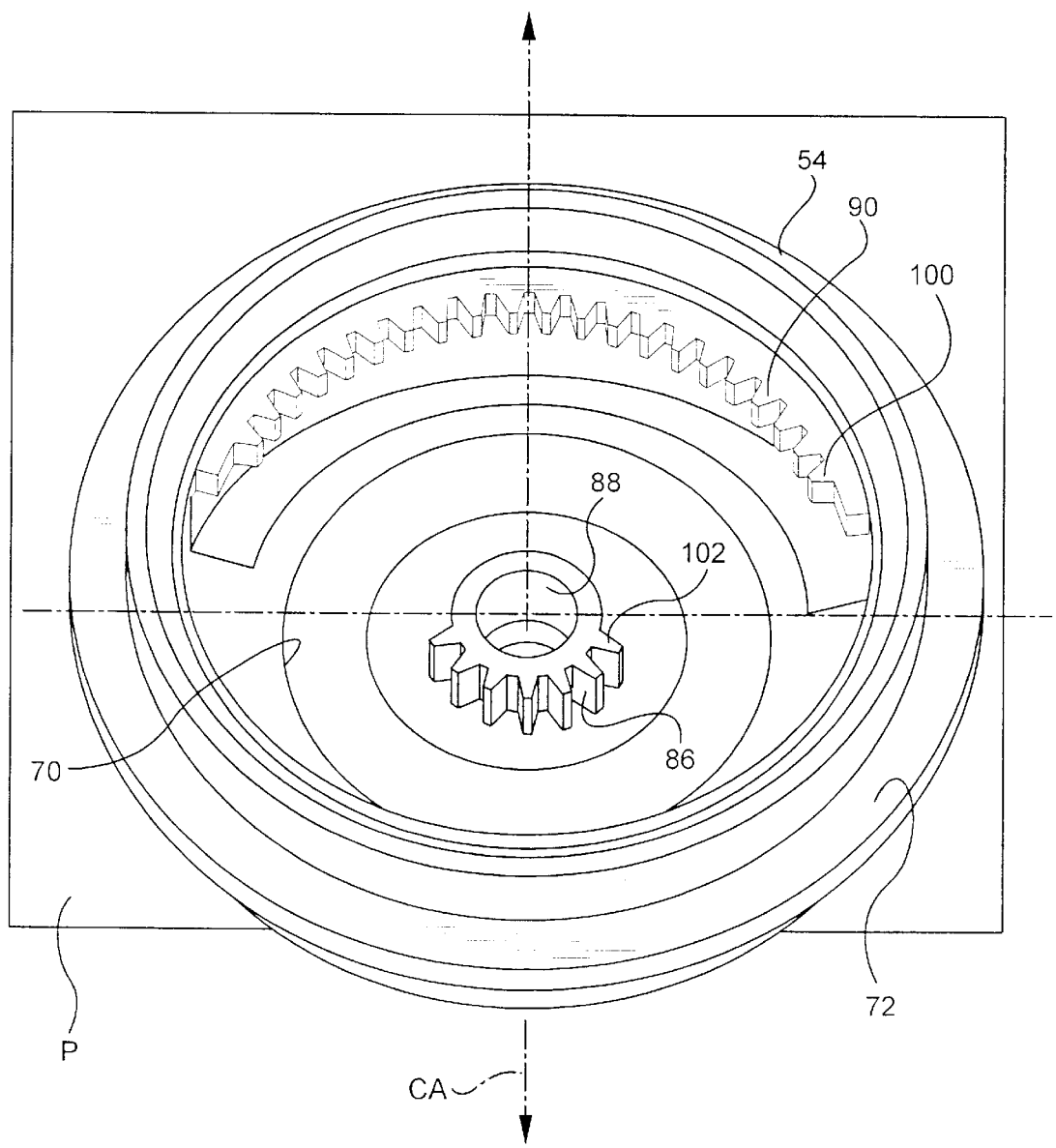
FIG. 17 is a bottom perspective view of the directional gear of the gear train of FIGS. 15 and 16.
Figure 18:
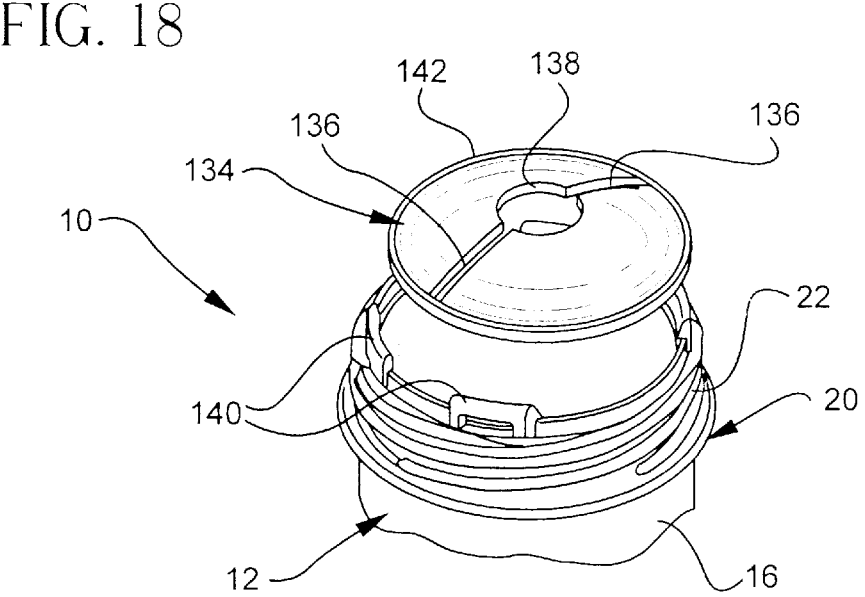
FIGS. 18–20 are fragmentary perspective views which show the blade wiping diaphragm of the mixing device of FIG. 1

Note that the central axis CA lies in a plane P which divides the directional gear 54 into a first directional gear side and a second directional gear side (see e.g. FIG. 17). Moreover, the directional gear 54 is configured so that (i) the gear teeth 86 are positioned entirely on the first input gear side, and (ii) the gear teeth 90 are positioned entirely on the second input gear side as shown in FIG. 17.

As shown in FIGS. 12–14, 15, and 16, the idler gear 56 has a number of gear teeth 92 defined therein, whereas the output pinion 48 has a number of gear teeth 94 defined therein. The gear teeth 92 of the idler gear 56 are meshingly engaged with the gear teeth 94 of the output pinion 48. As such, rotation of the idler gear 56 in a given direction causes rotation of the output pinion 48 in the opposite direction. For example, clockwise rotation of the idler gear 56 causes counterclockwise rotation of the output pinion 48, and vice versa.

As alluded to above, the gear teeth 92 of the idler gear 56 are engaged by either the inner gear teeth 86 or the outer gear teeth 90 of the directional gear 54 during rotation of the directional gear 54. Specifically, during rotation of the directional gear 54 in the counterclockwise direction (as viewed from the bottom perspective view of FIGS. 15–17 and designated by the arrow 96), the idler gear 56 is initially engaged by the outer gear teeth 90 of the directional gear 54 thereby causing the idler gear 56 to likewise be rotated in the counterclockwise direction (as indicated by the arrow 96). Rotation of the idler gear 56 in the counterclockwise direction causes rotation of the output pinion 48 (and hence the mixing blade 52) in the opposite direction (i.e. in a clockwise rotation as viewed from the bottom perspective view of FIGS. 15–17 and designated by the arrow 98).

Continued rotation of the crank 40 (and hence the directional gear 54) in the counterclockwise direction (as viewed from the bottom perspective view of FIGS. 15–17 and indicated by the arrow 96) causes the last gear tooth 100 of the outer gear teeth 90 to be rotated out of engagement with the idler gear 56 and a first tooth 102 of the inner gear teeth 86 to be rotated into meshing engagement with the idler gear 56. It should be appreciated that a small radial gap may be provided between the last gear tooth 100 of the outer gear teeth 90 and the first gear tooth 102 of the inner gear teeth 86 in order to prevent the idler gear 56 from being simultaneously engaged by both sets of gear teeth 86, 90.

In any event, as the inner gear teeth 94 meshingly engage the idler gear 56, the direction of travel of the idler gear 56 is changed. Specifically, when the directional gear 54 is rotated in the counterclockwise direction (as viewed from the bottom perspective view of FIGS. 15–17 and indicated by the arrow 96), meshing engagement with the inner gear teeth 94 causes the idler gear 56 to be rotated in the opposite direction (i.e. the clockwise direction as viewed from the bottom perspective view of FIGS. 15–17 and indicated by the arrow 94). Such clockwise rotation of the idler gear 56 causes the output pinion 48 (and hence the mixing blade 52) to be rotated in the opposite direction (i.e. the counterclockwise direction as viewed from the bottom perspective view of FIGS. 15–17 and indicated by the arrow 96).

Figure 15:
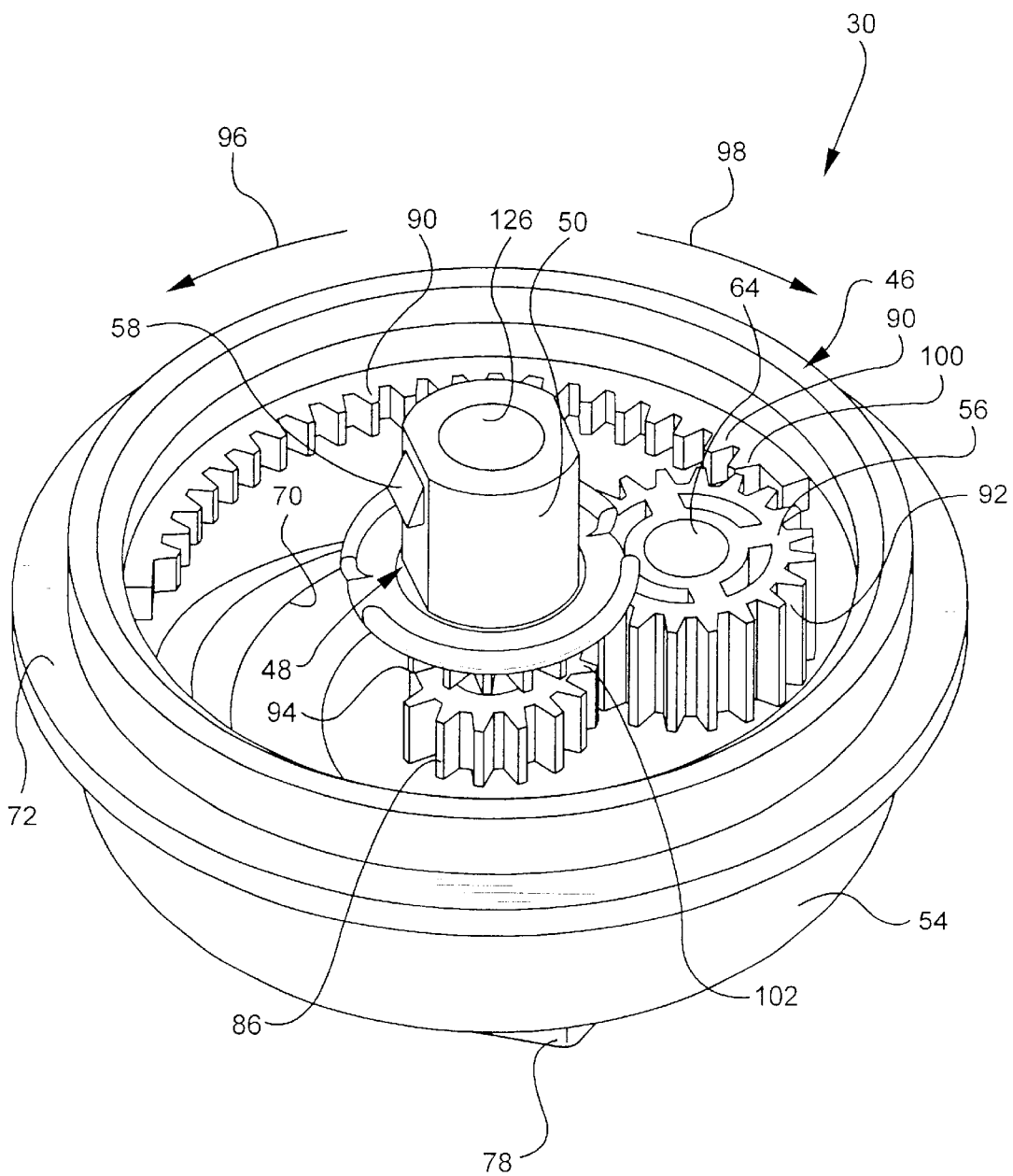
FIGS. 15 and 16 are bottom perspective views of the gear train of the mixing head assembly of FIGS. 12–14.
Figure 16:
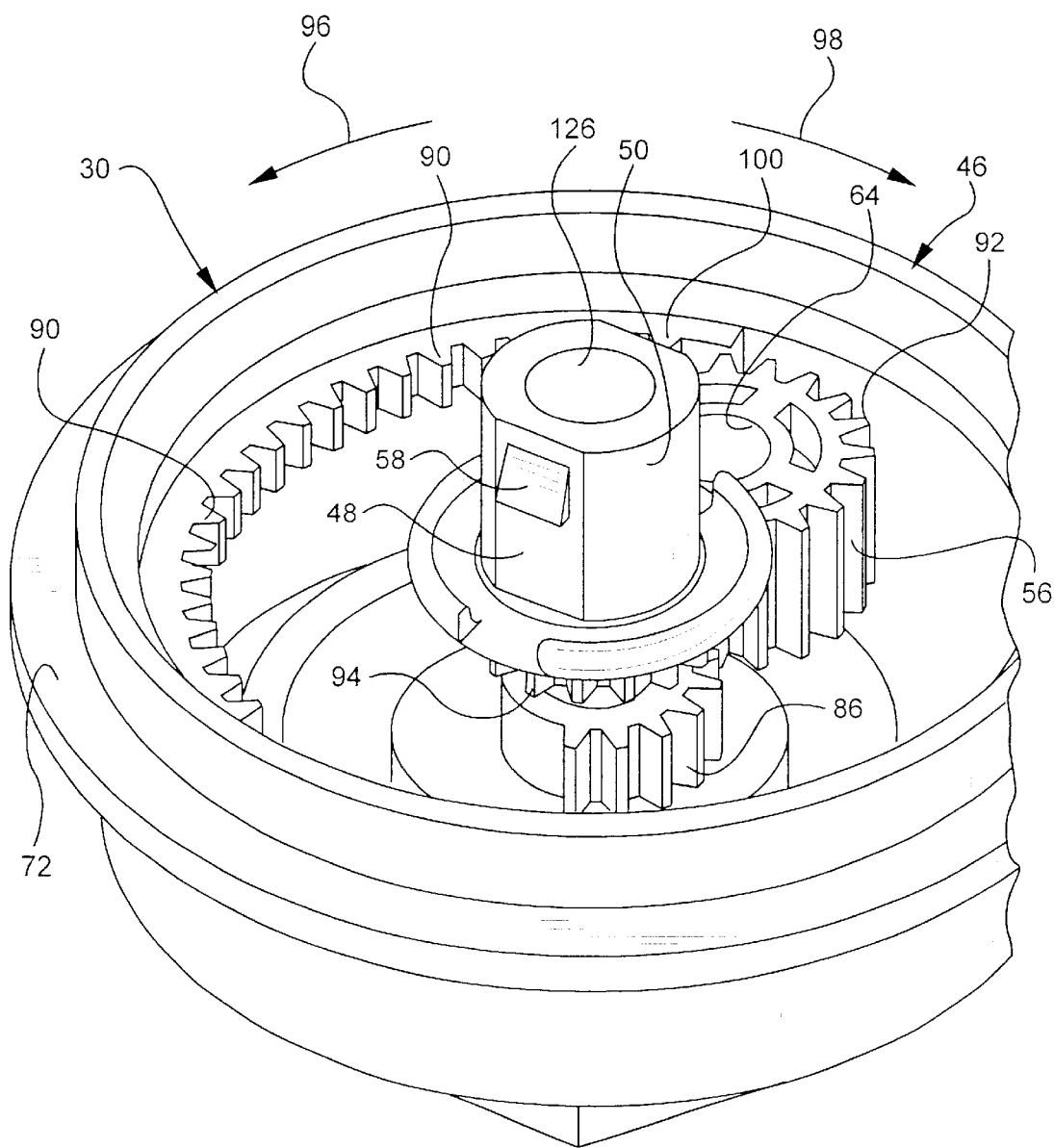

It should be appreciated that if the crank 40 is rotated in the opposite direction (i.e. so as to cause rotation of the directional gear 54 in the clockwise direction as viewed in FIGS. 15–17 and indicated by arrow 98), the idler gear 56 and the output pinion 48 are rotated in the respective opposite directions to that as described above. In particular, rotation of the directional gear 54 in the clockwise direction (i.e. in the direction of arrow 98 of FIGS. 15–17) causes (1) clockwise rotation of the idler gear 56, and (2) counterclockwise rotation of the output pinion 48 (and hence the mixing blade 52) when the idler gear 56 is meshingly engaged with the outer gear teeth 90. Similarly, rotation of the directional gear 54 in the clockwise direction (i.e. in the direction of arrow 98 of FIGS. 15–17) causes (1) counterclockwise rotation of the idler gear 56, and (2) clockwise rotation of the output pinion 48 (and hence the mixing blade 52) when the idler gear 56 is meshingly engaged with the inner gear teeth 86.

Hence, as described above, the gear train 46 of the present invention is configured such that the direction of rotation of the output pinion 48 changes despite rotation of the crank 40 in only a single direction. Specifically, as the idler gear 56 is engaged with the outer gear teeth 90, the output pinion 48 and hence the mixing blade 52 is rotated in a first direction. However, as the idler gear 56 disengages the outer gear teeth 90 and engages the inner gear teeth 86, the direction of travel of the output pinion 48 and hence the mixing blade 52 is reversed thereby creating alternating or reciprocating motion.

Moreover, since the relatively large number of individual gear teeth associated with the outer gear teeth 90 creates a relatively large gear ratio with the idler gear 56 relative to the gear ratio created by inner gear teeth 86 and the idler gear 56, varying angular distances of travel and speeds of the mixing blade 52 are created. Specifically, the relatively high gear ratio created by the outer gear teeth 90 causes the output pinion 48 to be driven across a greater angular distance when the idler gear 56 is engaged with the outer gear teeth 90 relative to the angular distance across which the output pinion 48 is driven when the idler gear 56 is engaged with the inner gear teeth 86. In one exemplary embodiment, the output pinion 48 (and hence the mixing blade 52) is driven across 540° of rotation when the idler gear 56 is engaged with the outer drive teeth 90, whereas the output pinion (and hence the mixing blade 52) is only advanced across 135° of rotation (in the opposite direction) when the idler gear 56 is engaged with the inner drive teeth 86. In other words, in such an exemplary embodiment, when an operator advances the crank 40 through an entire revolution (i.e. 360° of rotation), the mixing blade 52 is driven across 540° of rotation in a first direction and then reversed and driven across 135° of rotation in the opposite direction.

Moreover, the relatively high gear ratio created by the outer gear teeth 90 also causes the output pinion 48 to be driven at a greater angular velocity when the idler gear 56 is engaged with the outer gear teeth 90 relative to the angular velocity at which the output pinion 48 is driven when the idler gear 56 is engaged with the inner gear teeth 86. In one exemplary embodiment, when the idler gear 56 is engaged with the outer drive teeth 90, the output pinion 48 (and hence the mixing blade 52) is driven at a velocity which is approximately three times greater than the velocity at which the output pinion 48 (and hence the mixing blade 52) is driven when the idler gear 56 is engaged with the inner drive teeth 86. In other words, in such an exemplary embodiment, when an operator advances the crank 40 through an entire revolution (i.e. 360° of rotation), the mixing blade 52 is driven three times as quickly in the first direction as it is when reversed and driven in the opposite direction.

It should be appreciated that the configuration of the directional gear 54 described herein is exemplary in nature and may be altered to fit the requirements of a given design of the mixing device 10. In particular, it should be noted that the number of teeth included in the gear teeth 86 and 90 may be varied in order to produce a desired gear ratio. Such modification to the gear teeth 86 and 90 would allow for modification to the angular distance and speed at which the mixing blade 52 is driven during rotation of the crank 40 by the operator.

It should also be appreciated that the aforedescribed drive characteristics of the mixing head assembly 30 provide numerous advantages to the mixing device 10 of the present invention relative to heretofore designed mixing devices. For example, the aforedescribed reciprocating movement of the mixing blade 52 (i.e. at varying angular distances and speeds) creates desirable "agitation" within the mixing chamber 14 of the canister 12. Such agitation increases the mix quality of the mixing device 10 by reducing, if not eliminating, the amount of the powder component which is not thoroughly mixed with the liquid component.

Referring now to FIG. 7, the mixing blade 52 will be described in greater detail. The mixing blade 52 includes an elongated central shaft 104 having an upper end 106 which includes the coupling portion 108 for securing the shaft 104 of the blade 52 to the coupling portion 50 of the output pinion 48. The shaft 104 also has a lower end 108 which extends downwardly and into contact with a plunger 110. The plunger 110 is made from a plastic material such as polyethylene. The plunger 110 includes a recess 112 which receives a tip 114 of the shaft 104 thereby providing mechanical support for the shaft 104 during rotation thereof.

A number of blades or vanes 116 extend outwardly from the shaft 104 as shown in FIG. 7. The mixing blade 52 may be configured as a "two-dimensional" (i.e. flat) blade, or alternatively, may be configured as a "three dimensional" blade. Specifically, although the vanes 116 may be configured to extend outwardly in only two directions from the shaft 104, the vanes 116 of the mixing blade 52 may also be configured to extend outwardly from the shaft 104 in three directions. In such a three dimensional configuration, the mixing blade 52 is not substantially flat when positioned on a relatively flat surface, but rather extends in a number of different directions (including upwardly) from the flat surface.

Moreover, as shown in FIG. 7, the vanes 116 are oriented in somewhat of a helical configuration around the shaft 104. Such a configuration provides numerous advantages to the mixing device 10 of the present invention. For example, the helical configuration of the mixing blade 52 generates a desirable amount of "turbulence" within the mixing chamber 14 of the canister 12 thereby increasing the mixing efficiency of the mixing device 10.

The shaft 104 of the mixing blade 52 has an elongated fluid passageway 118 defined therein. The fluid passageway 118 extends from the upper end 106 of the shaft 104 to the lower end 108 of the shaft 104. The fluid passageway 118 is placed in fluid communication with the mixing chamber 14 of the canister 12 via a number of fluid orifices 120 defined in the shaft 104. While seven (7) fluid orifices 120 are shown defined in the shaft 104, it should be appreciated that there may be more than seven (7) fluid orifices defined in the shaft 104 (e.g. nine or ten fluid orifices). Alternatively, there may be less than seven (7) fluid orifices defined in the shaft 104 (e.g. two or three fluid orifices). The fluid passageway 118 and the fluid orifices 120 allow for the introduction of the liquid cement component (e.g. the monomer) without exposing the operator to any vapors or fumes from therefrom. In particular, as shown in FIG. 7, the crank 40 has a monomer delivery port 122 defined therein (see also FIG. 12). A tube 124 (see FIG. 7) is press fit into the lower end of the delivery port 122 and extends downwardly through the aperture 88 defined in the directional gear 54 and a similar aperture 126 defined in the output pinion 48 (see FIGS. 9, 12, 15, and 16). The lower end of the tube 124 is press fit or otherwise positioned in the coupling portion 108 of the mixing blade 52 so as to be in fluid communication with the fluid passageway 118 defined in the shaft 104.

Hence, a quantity of liquid cement component may be introduced into the mixing chamber 14 of the canister 12 through the delivery port 122. Specifically, the liquid cement component (e.g. the monomer) may be introduced into the mixing chamber 14 via a fluid path which includes the delivery port 122, the tube 124, the fluid passageway 118 of the shaft 104, and the fluid orifices 120 of the shaft 104. In such a manner, the monomer may be delivered at various locations throughout the depth of the powder component which is present in the mixing chamber 14. In particular, since the fluid orifices 120 are provided at a number of different locations along the length of the shaft 104, the liquid component (e.g. the monomer) is delivered at locations throughout the height of the canister 12 thereby allowing the liquid to be interspersed throughout the powder component present in the mixing chamber 12. This is a significant advantage over heretofore designed systems in which the monomer is poured or otherwise advanced through the lid of the mixing apparatus thereby only allowing the monomer to be introduced to the "top" of the powder within the mixing apparatus. Moreover, the structure of the present invention also provide advantages over heretofore designed systems having a delivery path through the mixing shaft of the system which have an opening only at the bottom end of the shaft (similar to a common drinking straw). In such a configuration, the monomer flows only out of the bottom of the shaft and in some cases may be restricted by the plunger on which the lower end of the shaft rests.

It should be appreciated that the monomer delivery port 122 may be embodied to include a luer lock that is configured such that a luer or similar spout from a monomer delivery device (not shown) may be extended into sealing engagement therewith. The use of such a luer lock allows monomer to be dispensed into tube 124 (and hence the mixing chamber 14 of the canister 12) while preventing monomer vapors from escaping between the monomer delivery device and the mixing device 10 (i.e. between luer of the delivery device and the luer lock of the mixing device).

It should be appreciated that such a luer lock may be configured to facilitate a "slip fit" type of sealing arrangement, or, alternately, may be configured to facilitate a threaded coupling with the corresponding mechanism of the monomer delivery device. Moreover, a combination coupling mechanism may be utilized which facilitates mating with both threaded and non-threaded couplings.

A cap 128 is provided to selectively seal the delivery port 122. Specifically, the cap 128 may be sealing received into the delivery port 122 in order to seal the delivery port 122 in a manner which prevents vapors or the like from escaping therefrom. A tether 130 extends between the crank 40 and the cap 128 in order to movably secure the cap 128 to the crank 40.

As alluded to above, the cap 128 is used to seal delivery port 122 after the monomer has been dispensed into mixing chamber 14 during the mixing process. The cap 128 is shown in a disengaged position in FIG. 7 in anticipation of the coupling of the monomer delivery device (not shown) with the delivery port 122 for the purpose of delivering monomer from the monomer delivery device into the mixing chamber 14. It will be appreciated that a variety of luer locks and luer lock caps may be used in the present invention. For example, a self-closing luer lock may be used thereby eliminating the need for luer cap 128 or, as described above, a threaded luer lock may be used to screw the cap 128 onto the body of the crank 40. In another embodiment, the monomer delivery device itself may be used as a seal for the luer lock. In yet another embodiment, the luer cap 128 may be replaced with a paper-backed piece of re-sealable tape or the like which may be removed to allow for mating with the monomer delivery device, and then replaced when the monomer delivery device is detached.

Referring now to FIG. 9, the lower gear housing 38 has a vacuum port 132 defined therein (see also FIG. 1). A vacuum source (not shown) may be fluidly coupled to the vacuum port 132 in order to draw air from the mixing chamber 14 of the mixing device 10. The introduction of a vacuum is useful during the aforedescribed introduction of the liquid cement component into the mixing chamber 14 since the presence of lower pressure within the chamber 14 tends to draw the liquid (i.e. the monomer) through the fluid orifices 120 of the shaft 104 and into the mixing chamber 14. Moreover, the presence of the vacuum also removes vapors and the like from the mixing device 10 thereby further reducing the occasions in which such vapors escape from the device 10.

As shown in FIGS. 7, 9, 18–22, the mixing device 10 also includes a blade wiping member or diaphragm 134. The blade wiping diaphragm 134 is preferably constructed of an elastomeric material. The blade wiping diaphragm 134 has a number of vane receiving slots 136 and a shaft receiving opening 138 defined therein. As will now be described in greater detail, the blade wiping diaphragm 134 is provided to "wipe" or otherwise remove residual bone cement for the mixing blade 52 during removal thereof from the mixing chamber 14. As such, the blade wiping diaphragm 134 may be configured to include any number, size, or shape of vane receiving slots 136 in order to accommodate a given design of a mixing blade 52.

Figure 19:
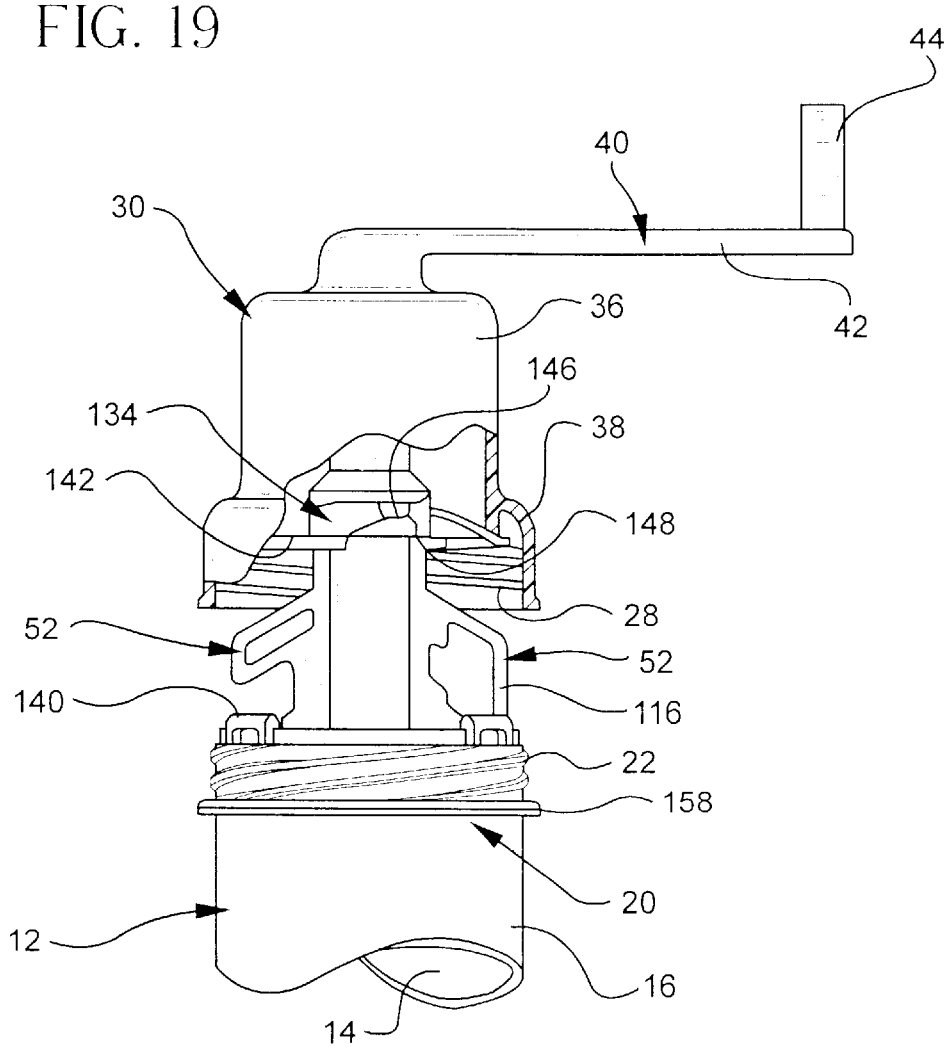
Figure 20:
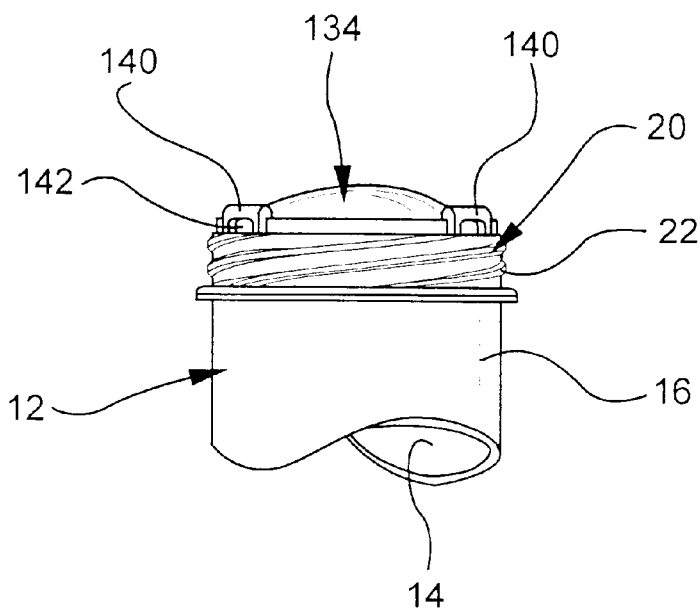

Once the liquid bone cement component (e.g. the monomer) and the powder bone cement component have been thoroughly mixed with one another, the lower gear housing 38 is unscrewed from the cartridge 16 so that the mixing head assembly 30 may be removed from the cartridge 16 thereby allowing a delivery nozzle assembly 150 (see FIGS. 23 and 24) to be screwed onto the cartridge 16 in its place. During such removal of the mixing head assembly 30, as shown in FIG. 19, the vanes 116 of the mixing blade 52 are advanced through the vane receiving slots 136 of the blade wiping diaphragm 134. Such advancement of the vanes 116 through the vane receiving slots 136 wipes or otherwise removes any residual bone cement from the vanes 116 thereby preventing such residual bone cement from being wasted (i.e. removed from the mixing chamber 14, but not utilized in the surgical procedure).

Figure 21:
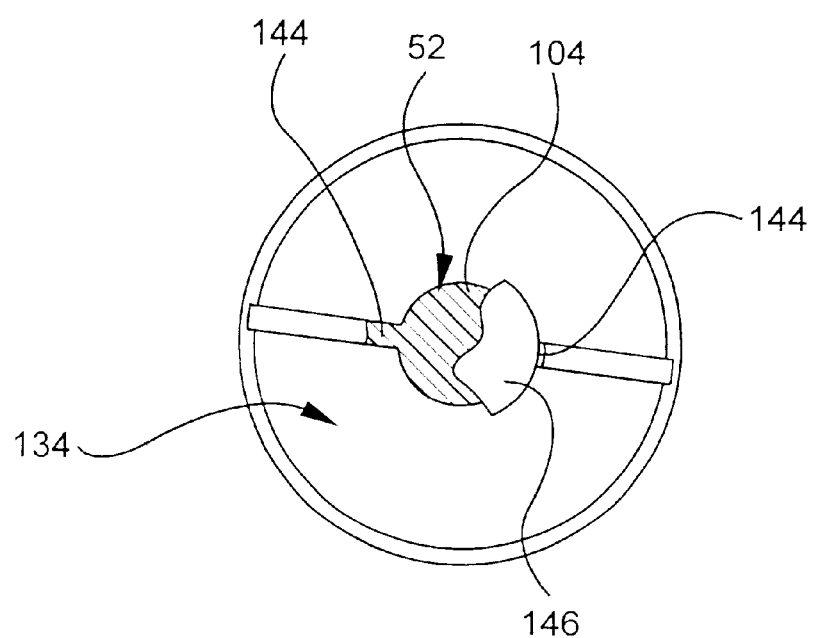
FIG. 21 is fragmentary plan view of the blade wiping diaphragm of FIGS. 18–20 and the mixing blade of FIG. 7.
Figure 22:
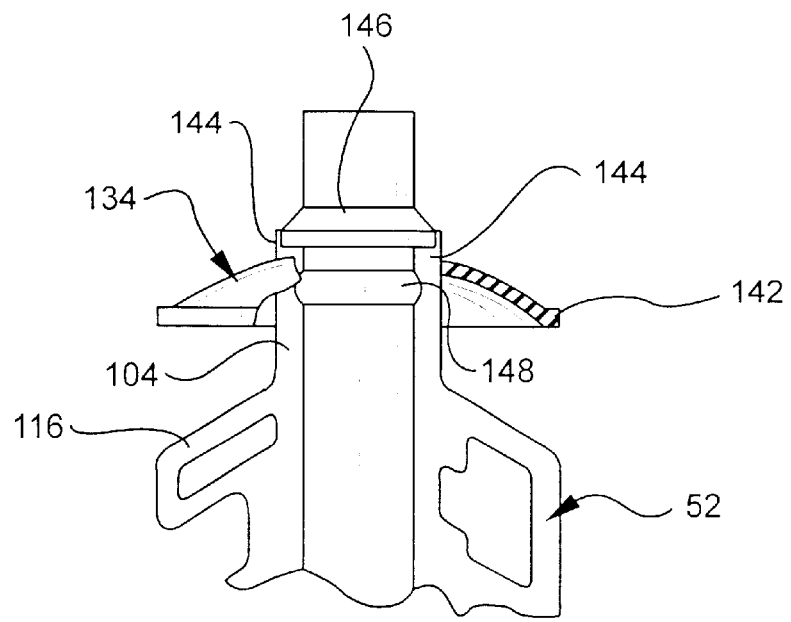
FIG. 22 is a fragmentary side elevational view of the blade wiping diaphragm of FIGS. 18–20 and the mixing blade of FIG. 7.

In order to provide for proper alignment of the vanes 116 of the mixing blade 52 with the vane receiving slots 136, the blade wiping diaphragm 134 is rotatably secured to the cartridge 16. In particular, as show in FIG. 18, the cartridge 16 includes a number of retaining members or snaps 140. An outer peripheral edge 142 of the blade wiping diaphragm 134 is positioned under the snaps 140 in order to secure the diaphragm 134 to the cartridge 16 during securement of the mixing head assembly 30 to the cartridge 16. Moreover, the mixing blade 52 is preferably configured to include a number of protrusions or "wings" 144 which extend outwardly from the shaft 104 (see FIGS. 21 and 22). The wings 144 are aligned with the vanes 116 and are therefore positioned in the vane receiving slots 136 as shown in FIGS. 21 and 22. As such, rotation of the mixing blade 52, and therefore the wings 144, causes similar rotation of the blade wiping diaphragm 134.

Moreover, the wings 144 also function to retain the blade wiping diaphragm 134 on the mixing blade 52 prior to securement of the mixing head assembly 30 to the cartridge 16. In particular, the blade wiping diaphragm 134 is initially secured to the wings 144 of the mixing blade 52 prior to use of the mixing device 10. In such a manner, as shall be discussed below in greater detail, the powder bone cement component may be poured or otherwise advanced into the open end (i.e. the upper end 20) of the cartridge 16. Once the powder component has been poured into the open end of the cartridge 16, the mixing head assembly 30 is screwed onto the threads 22 of the upper end 20 of the cartridge 16. As the mixing head is screwed onto the upper end 20 of the cartridge 16, the outer peripheral edge 142 of the blade wiping diaphragm 134 is pressed or otherwise advanced under each of the snaps 140 in order to secure the diaphragm 134 to the cartridge 16. As shall be discussed below in greater detail, such positioning of the outer peripheral edge 142 of the blade wiping diaphragm 134 under the snaps 140 allows for retention of the blade wiping diaphragm 134 during subsequent removal of the mixing head assembly 30.

It should be appreciated that the configuration of the mixing device 10 in which the blade wiping diaphragm 134 is rotated in concert with the mixing blade 52 reduces the number of vane receiving slots 136 that must be included in the construction of the blade wiping diaphragm 134. Specifically, since the wings 144 are retained in the slots 136, the vanes 116 (which are aligned with the wings 144) are likewise at all times aligned with the vane receiving slots 136. Hence, at any given time, the mixing blade 52 may be removed by pulling the vanes 116 of the blade 52 through the vane receiving slots 136. Such a reduction in the number of vane receiving slots 136 facilitates ease of manufacture of the blade wiping diaphragm 134.

As shown in FIG. 22, the shaft 104 of the mixing blade 52 also has an upper shoulder 146 and a lower shoulder 148 defined therein. As shown in FIG. 22, the body of blade wiping diaphragm 134 is captured or otherwise positioned between the upper shoulder 146 and the lower shoulder 148. The upper shoulder 146 is greater in diameter than the lower shoulder 148. The upper shoulder prevents upward movement of the blade wiping diaphragm 134. The lower shoulder 148, on the other hand, is somewhat smaller in diameter and includes a number of rounded edges. In such a manner, the lower shoulder 148 supports the blade wiping diaphragm 134 in its desired position, but also allows for removal of the mixing blade 52 since the lower shoulder may be advance through the shaft receiving opening 138 of the blade wiping diaphragm 134 during removal of the blade 52.

Figure 23:
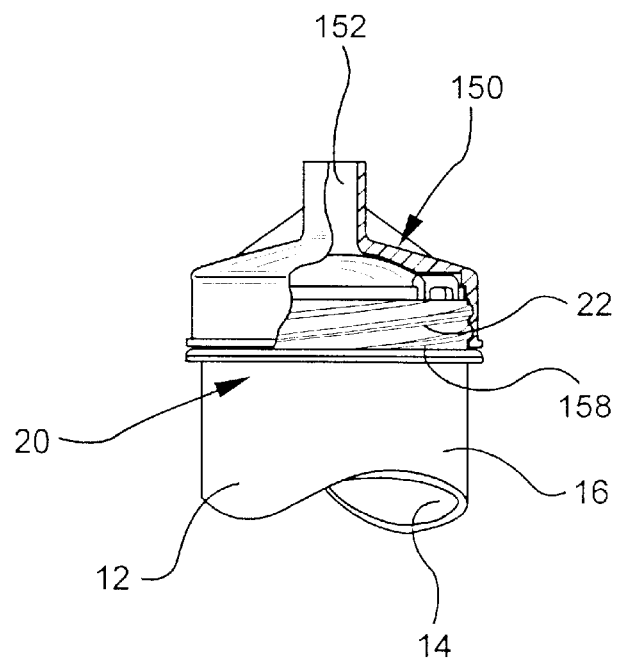
FIGS. 23 and 24 are fragmentary perspective views of the mixing device of FIG. 1 with the cement delivery nozzle secured thereto.
Figure 24:
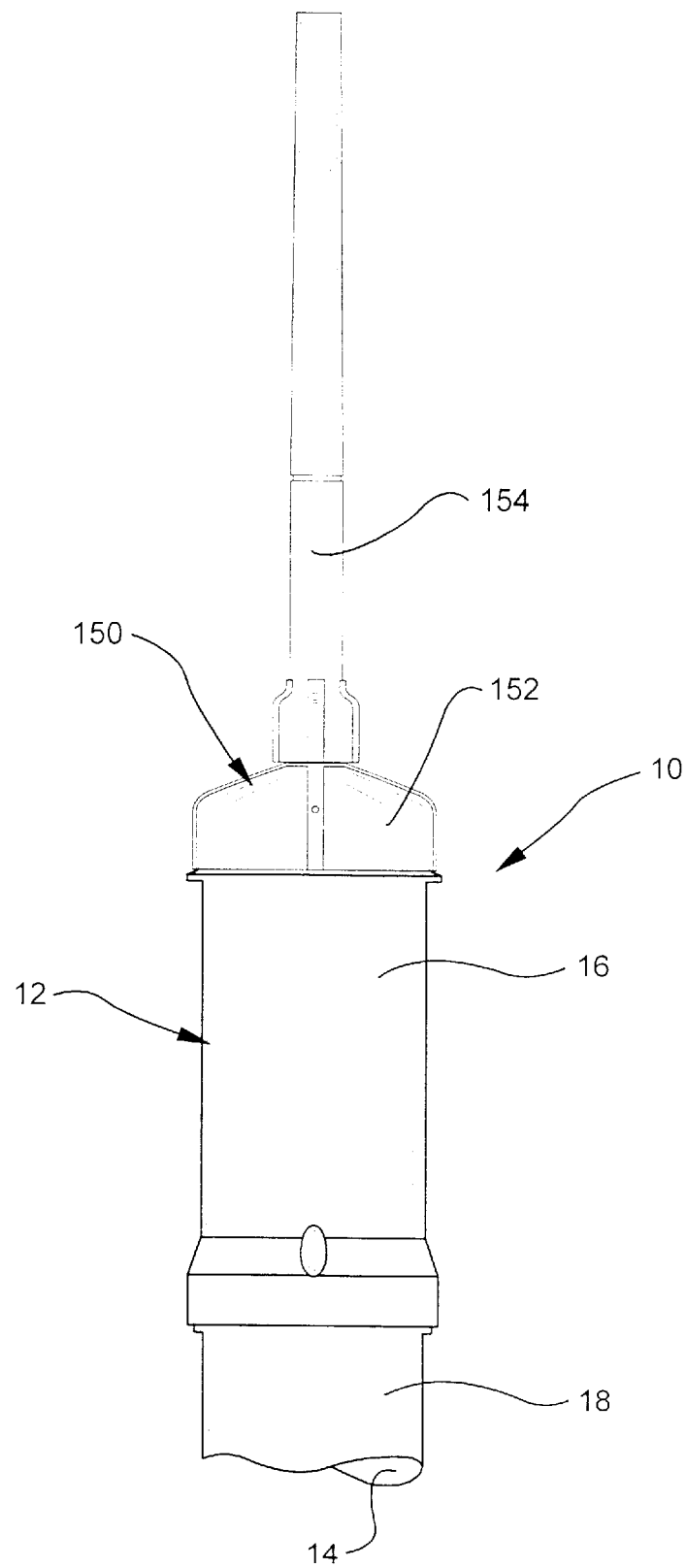
Figure 25:
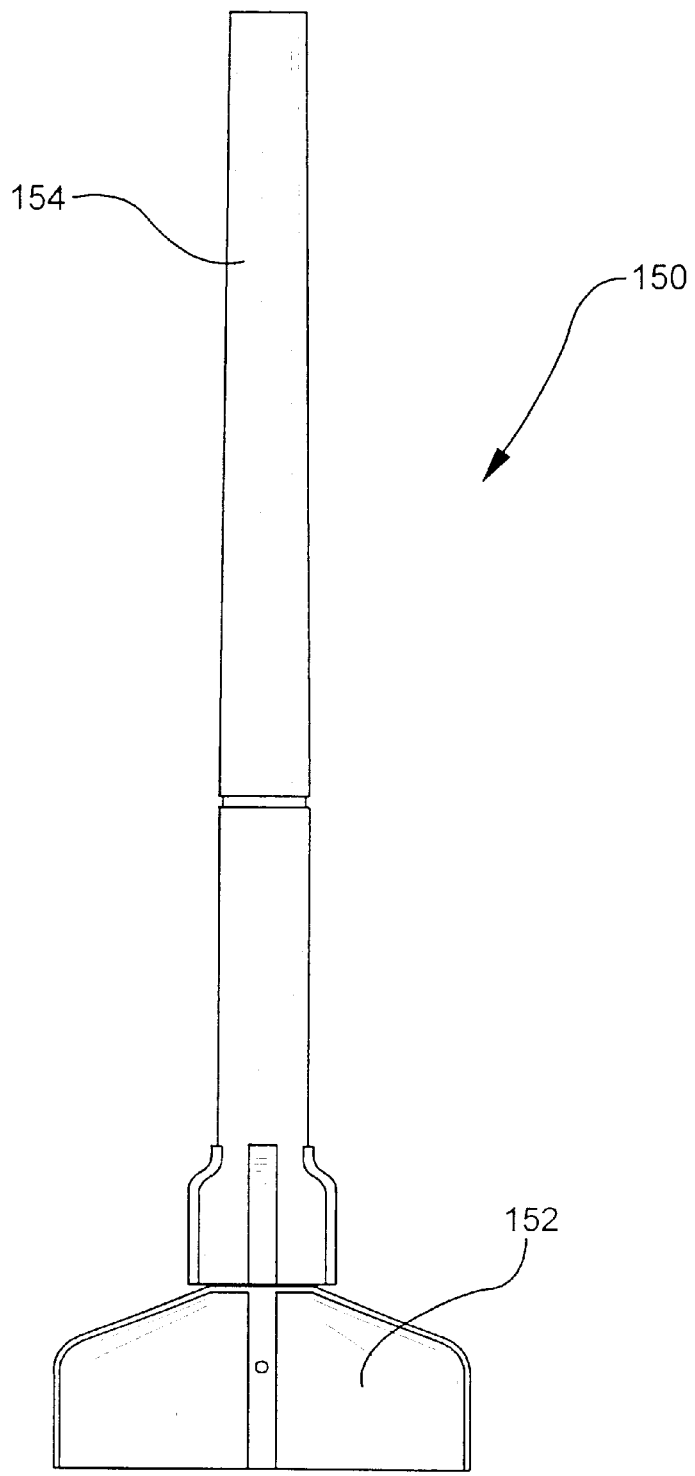
FIG. 25 is an enlarged view of the cement delivery nozzle of FIGS. 23 and 24.

As alluded to above, once the liquid cement component and the powder cement component have been thoroughly mixed, the mixing device 10 of the present invention may be utilized to deliver the mixed bone cement. In particular, as shown in FIGS. 23–25, once the liquid bone cement component (e.g. the monomer) and the powder bone cement component have been thoroughly mixed with one another, the lower gear housing 38 is unscrewed from the cartridge 16 so that the mixing head assembly 30 may be removed from the cartridge 16. Thereafter, the delivery nozzle assembly 150 may be screwed onto the threads 22 of the upper end 20 of the cartridge 16. The nozzle assembly 150 includes a nozzle 152 and an elongated tube 154. It should be appreciated that the length and/or diameter of the elongated tube 154 may be varied in order to fit the requirements of a given delivery application. Moreover, it should also be noted that in certain situations, it may be desirable to dispense (i.e. delivery) the mixed bone cement directly through the nozzle 152 without the use of the elongated tube 154.

In any event, once the nozzle assembly 150 has been secured to the canister 12, the lower end 24 of the cartridge 18 is unscrewed from the base 34 thereby separating the canister 12 from the base 34. Such removal of the base 34 also exposes a bottom surface 156 of the plunger 110 (see FIG. 7). The canister 12 may then be placed in the chamber of a delivery gun mechanism (not shown) much in the same way as a tube of caulk is placed in a household caulk gun. As the operator squeezes the trigger (not shown) or otherwise actuates the gun mechanism, a contact member (not shown) urges the plunger 110 in the general direction toward the nozzle assembly 150. Such movement of the plunger 110 forces the mixed bone cement within the mixing chamber 14 through the openings defined in the blade wiping diaphragm 134 (i.e. the vane receiving slots 136 and the shaft receiving opening 138) and then through the nozzle 152 and tube 154 of the nozzle assembly.

Operation of the Present Invention

In operation, the bone cement mixing device 10 of the present invention is utilized to mix a liquid bone cement component with a powder bone cement component and thereafter deliver the mixed bone cement to a desired location during performance of a surgical procedure. In order to do so, the powder bone cement component is first placed in the mixing chamber 14 of the canister 12. In particular, with the mixing head assembly 30 removed from the canister 12, a quantity of the powder bone cement component is poured or otherwise advanced into the open end of the cartridge 16 (i.e. the upper end 20 of the cartridge 16) and hence into the mixing chamber 14 of the canister 12. As discussed above, the canister 12 is preferably configured to accommodate (i.e. hold) at least 120 grams (e.g. three batches of 40 grams each) of powder bone cement.

Once the powder bone cement component has been placed in the canister 12, the mixing head 30 is screwed onto the upper end 20 of the cartridge 16. In particular, as shown in FIG. 7, the threads 28 of the lower gear housing 38 are threadingly advanced onto the threads 22 of the upper end 20 of the cartridge 16 until the mixing head 30 is fully secured to the canister 12. As discussed above, as the mixing head assembly is screwed onto the upper end of the cartridge 16, the O-ring 158 is compressed thereby sealing the mixing head 30 to the canister 12 (see FIG. 19).

Moreover, during such attachment of the mixing head 30 to the canister 12, the blade wiping diaphragm 134 (which is secured to the wings 144 of the mixing blade 52) is secured to the canister 12. In particular, as the mixing head assembly 30 is screwed onto the canister 12, the outer peripheral edge 142 of the blade wiping diaphragm 134 is pressed or otherwise advanced under the snaps 140 of the cartridge 16 thereby securing the diaphragm 134 to the cartridge 16.

Once the mixing head assembly 30 is sealingly secured to the canister 12 in such a manner, the liquid bone cement component (e.g. the monomer) may be advanced into the mixing chamber 12 and hence into contact with the powder bone cement component positioned therein. In particular, as shown in FIG. 7, the port cap 128 is first removed from sealing engagement with the monomer delivery port 122 in order to permit fluid access to the mixing chamber 14 of the canister 12. Thereafter, the required quantity of liquid cement component may be introduced into the mixing chamber 14 of the canister 12 through the delivery port 122. Specifically, an outlet coupling of a monomer delivery device (not shown) is first sealingly coupled to the monomer delivery port 122 of the mixing device 10. Thereafter, the liquid cement component (e.g. the monomer) contained in the monomer delivery device is introduced into the mixing chamber 14 via the fluid path which includes the delivery port 122, the tube 124, the fluid passageway 118 of the shaft 104, and the fluid orifices 120 of the shaft 104. In such a manner, the monomer is delivered at various locations throughout the depth of the powder component present in the mixing chamber 14. In particular, since fluid orifices 120 are provided at a number of different locations along the length of the shaft 104, the liquid component (e.g. the monomer) is delivered at locations throughout the height of the canister 12 thereby allowing the liquid to be interspersed throughout the depth of the powder component present in the mixing chamber 12.

It should be appreciated that since the monomer delivery port 122 is preferably embodied as a luer lock or other type of sealable component, and therefore "mated" with a similar type of outlet coupling on the monomer delivery device, the monomer is dispensed into the tube 124 (and hence the mixing chamber 14 of the canister 12) while preventing monomer vapors from escaping between the monomer delivery device and the mixing device 10 (e.g. between luer of the monomer delivery device and the luer lock of the mixing device 10).

It should be appreciated that, as described above, it may be desirable to introduce the monomer into the mixing chamber 14 of the canister 12 in the presence of a vacuum within chamber 14. In such a case, a vacuum source (not shown) is fluidly coupled to the vacuum port 132 of the lower gear housing 38 of the mixing head assembly 30 in order to draw air from the mixing chamber 14 of the mixing device 10. The introduction of a vacuum is useful during the aforedescribed introduction of the liquid cement component into the mixing chamber 14 since the presence of lower pressure within the chamber 14 tends to draw the liquid (i.e. the monomer) through the fluid orifices 120 of the shaft 104 and into the mixing chamber 14. Moreover, the presence of the vacuum also removes vapors and the like from the mixing device 10 thereby further reducing the occasions in which such vapors escape from the device 10. However, in certain applications, it may be desirable to introduce the liquid monomer into the mixing chamber 14 without the presence of a vacuum within the canister 12.

In any event, after the monomer has been dispensed into mixing chamber 14 in the manner described above, the cap 128 is positioned back in sealing engagement within the delivery port 122 so as to prevent the escape of any vapors associated with the delivered monomer. Thereafter, the operator may commence to mix the liquid cement component and the powder cement component with one another.

Specifically, the operator grips the outer surface of the canister 12 with one hand while gripping the knob 44 of the crank 40 with the other hand. The operator then rotates the crank 40 in either a clockwise or counterclockwise direction. Such rotation of the crank 40 drives the gear train 46 of the mixing head assembly 30. As described in detail above, the gear train 46 of the present invention is configured such that the direction of rotation of the output pinion 48 (and hence the mixing blade 52) alternates (i.e. changes) despite rotation of the crank 40 (and hence the directional gear 54) in only a single direction. Specifically, as shown in FIGS. 12–17, as the idler gear 56 is engaged with the outer gear teeth 90 of the directional gear 54, the output pinion 48 and hence the mixing blade 52 is rotated in a first direction. However, as the idler gear disengages the outer gear teeth 90 and engages the inner gear teeth 86 of the directional gear 54, the direction of travel of the output pinion 48 and hence the mixing blade 52 is reversed thereby creating alternating or reciprocating motion.

Moreover, as described above in greater detail, since the relatively large number of individual gear teeth associated with the outer gear teeth 90 creates a relatively large gear ratio with the idler gear 56 relative to the gear ratio created by inner gear teeth 86 and the idler gear 56, varying angular distances of travel and speeds of the mixing blade 52 are created. For example, in the case of the exemplary embodiment described herein, as the operator advances the crank 40 through an entire revolution (i.e. 360° of rotation), the mixing blade 52 is driven across 540° of rotation in a first direction and then reversed and driven across 135° of rotation in the opposite direction. Moreover, in such an exemplary embodiment, when as the operator advances the crank 40 through such an entire revolution (i.e. 360° of rotation), the mixing blade 52 is driven three times as quickly in the first direction as it is when reversed and driven in the opposite direction. Such a reciprocating movement of the mixing blade 52 (i.e. at varying angular distances and speeds) creates desirable "agitation" within the mixing chamber 14 of the canister 12 which increases the mix quality of the mixing device 10 by reducing, if not eliminating, the amount of the powder component bone cement which is not thoroughly mixed with the liquid component of the bone cement.

Moreover, as described above in greater detail, during such movement (i.e. rotation) of the mixing blade 52, the blade wiping diaphragm 134 is likewise rotated. In particular, in order to provide for proper alignment of the vanes 116 of the mixing blade 52 with the vane receiving slots 136 of the blade wiping diaphragm 134 during subsequent removal of the mixing head assembly 30 from the canister 12, the blade wiping diaphragm 134 is rotatable relative to the cartridge 16. Specifically, as show in FIG. 18, the outer peripheral edge 142 of the blade wiping diaphragm 134 is positioned under the snaps 140 in order to secure the diaphragm 134 to the cartridge 16 in a manner which allows the diaphragm to rotate relative to the cartridge 16. The wings 144 of the mixing blade 52 are positioned in the vane receiving slots 136 thereby causing the blade wiping diaphragm 134 to be rotated in concert with the mixing blade 52.

Once the liquid bone cement component (e.g. the monomer) and the powder bone cement component have been thoroughly mixed with one another, the mixing head assembly 30 is removed from the canister 12. In particular, the lower gear housing 38 is unscrewed from the cartridge 16 so that the mixing head assembly 30 may be removed from the cartridge 16 thereby allowing the delivery nozzle assembly 150 (see FIGS. 23 and 24) to be screwed onto the cartridge 16 in its place. During such removal of the mixing head assembly 30, as shown in FIG. 19, the vanes 116 of the mixing blade 52 are advanced through the vane receiving slots 136 of the blade wiping diaphragm 134. In particular, since the blade wiping diaphragm 134 is secured to the cartridge 16 by the snaps 140, the mixing blade 52 may be "pulled through" the openings (i.e. the vane receiving slots 136 and the shaft receiving opening 138) defined in the blade wiping diaphragm 134 without removing the blade wiping device. Such advancement of the vanes 116 through the vane receiving slots 136 wipes or otherwise removes any residual bone cement from the vanes 116 thereby preventing such residual bone cement from being wasted (i.e. removed from the mixing chamber 14, but not utilized in the surgical procedure).

The mixing device 10 of the present invention may be utilized to deliver the mixed bone cement. In particular, as shown in FIGS. 23–25, once the liquid bone cement component (e.g. the monomer) and the powder bone cement component have been thoroughly mixed with one another, the lower gear housing 38 is unscrewed from the cartridge 16 so that the mixing head assembly 30 may be removed from the cartridge 16. Thereafter, the delivery nozzle assembly 150 is screwed onto the threads 22 of the upper end 20 of the cartridge 16. The lower end 24 of the cartridge 18 is then unscrewed from the base 34 thereby separating the canister 12 from the base 34. As described above and shown in FIG. 7, such removal of the base 34 also exposes the bottom surface 156 of the plunger 110. The canister 12 may then be placed in the chamber of a delivery gun mechanism (not shown) much in the same way as a tube of caulk is placed in a household caulk gun. As the operator squeezes the trigger (not shown) or otherwise actuates the gun mechanism, a contact member (not shown) urges the plunger 110 in the general direction toward the nozzle assembly 150. Such movement of the plunger 110 forces the mixed bone cement within the mixing chamber 14 through the openings defined in the blade wiping diaphragm 134 (i.e. the vane receiving slots 136 and the shaft receiving opening 138) and then through the nozzle 152 and tube 154 of the nozzle assembly 150 thereby delivering the mixed bone cement to a desired location.

Hence, as described herein, bone cement mixing device 10 of the present invention provide numerous advantages over heretofore designed mixing apparatus. For example, the alternating or reciprocating action of the mixing blade 52 enhances the quality of the mixed bone cement by reducing, if not eliminating, the amount of powder component which is not adequately mixed with the liquid component. Moreover, such alternating or reciprocating action is advantageously generated by rotation of the crank 40 in only a single direction and at a single speed. In particular, the configuration of the gear train 46 eliminates the need for the operator to manually reverse the direction of the crank 40 and/or manually alter the speed at which the crank 40 is being rotated in order to produce the desired blade movement.

Yet further, the sealed relationship between the outlet coupling of the monomer delivery device and the delivery port 122 of the mixing device 10 provides for delivery and mixing of the bone cement without exposing the operator of the system to monomer vapors.

In addition, since the fluid orifices 120 of the mixing blade 52 are provided at a number of different locations along the length of the shaft 104, the liquid component (e.g. the monomer) is delivered at locations throughout the height of the canister 12 thereby allowing the liquid to be interspersed throughout the entire depth of the powder component present in the mixing chamber 12. As described above, this is a significant advantage over heretofore designed systems in which the monomer is poured or otherwise advanced through the lid of the mixing apparatus thereby only allowing the monomer to be introduced to the "top" of the powder within the mixing apparatus. Moreover, the structure of the present invention also provide advantages over heretofore designed system having a delivery path through the mixing shaft of the system which have an opening only at the bottom end of the shaft (similar to a common drinking straw). In such a configuration, the monomer only flows out of the bottom of the shaft and in some cases may be restricted by the plunger on which the lower end of the shaft rests.

While the invention has been illustrated and described in detail in the drawings and foregoing description, such an illustration and description is to be considered as exemplary and not restrictive in character, it being understood that only the preferred embodiments have been shown and described and that all changes and modifications that come within the spirit of the invention are desired to be protected.

There are a plurality of advantages of the present invention arising from the various features of the bone cement mixing and delivery device and associated method described herein. It will be noted that alternative embodiments of the bone cement mixing and delivery device and associated method of the present invention may not include all of the features described yet still benefit from at least some of the advantages of such features. Those of ordinary skill in the art may readily devise their own implementations of a bone cement mixing and delivery device and associated method that incorporate one or more of the features of the present invention and fall within the spirit and scope of the present invention.

What is claimed is:

1. A bone cement mixing apparatus, comprising:
   a handle;
   a canister defining a mixing chamber; and
   a mixing blade which is caused to rotate in response to movement of said handle, said mixing blade being positioned within said mixing chamber,
   wherein said mixing blade includes a shaft and at least one vane supported by said shaft, and
   wherein said shaft has defined therein (i) an inlet orifice, (ii) a plurality of outlet orifices, and (iii) a passageway which places said inlet orifice in fluid communication with each of said plurality of outlet orifices.

2. The bone cement mixing apparatus of claim 1, wherein:
   said shaft has an upper half segment and a lower half shaft segment, and
   at least one of said plurality of outlet orifices is defined in said upper half segment.

3. The bone cement mixing apparatus of claim 1, wherein:
   said shaft has an upper half segment and a lower half shaft segment,
   at least a first pair of said plurality of outlet orifices is defined in said upper half segment, and
   at least a second pair of said plurality of outlet orifices is defined in said lower half segment.

4. The bone cement mixing apparatus of claim 3, wherein:
   each of said first pair of said plurality of outlet orifices is vertically spaced apart from each other along the length of said shaft, and
   each of said second pair of said plurality of outlet orifices is vertically spaced apart from each other along the length of said shaft.

5. The bone cement mixing apparatus of claim 1, wherein:
   said shaft has a distal end, and
   at least one of said plurality of outlet orifices is spaced apart from said distal end of said shaft.

6. The bone cement mixing apparatus of claim 1, wherein:
   said plurality of outlet orifices includes at least seven outlet orifices, and
   each outlet orifice of said at least seven outlet orifices is vertically spaced apart from each other along the length of said shaft.

7. The bone cement mixing apparatus of claim 1, further comprising:
   a gear assembly having a plurality of mixing gears which are caused to rotate in response to movement of said handle, said mixing blade being caused to rotate in response to rotation of said mixing gears of said gear assembly;
   a fluid tube which extends through said gear assembly, said fluid tube being in fluid communication with said inlet orifice of said shaft.

8. The bone cement mixing apparatus of claim 7, wherein:
   said handle has a fluid delivery port defined therein, and
   said fluid tube is in fluid communication with said fluid delivery port.

9. The bone cement mixing apparatus of claim 7, wherein said tube extends through at least one of said plurality of mixing gears.

10. A method of mixing bone cement, comprising the steps of:
    placing a powder bone cement component within a canister;
    sealing the canister after the placing step;
    advancing a liquid bone cement component through a mixing blade located within the canister after the sealing step; and
    rotating the mixing blade after the liquid bone cement component is advanced through the mixing blade,
    wherein the mixing blade includes (i) an inlet orifice, (ii) a plurality of outlet orifices, and (iii) a passageway which places the inlet orifice in fluid communication with each of the plurality of outlet orifices, and
    wherein the advancing step includes the step of advancing the liquid bone cement component (i) into the mixing blade through the inlet orifice, (ii) through the passageway, and (iii) out of the mixing blade through the plurality of outlet orifices.

11. The method of claim 10, wherein:
    said mixing blade has an upper half portion and a lower half shaft portion, and
    at least one of said plurality of outlet orifices is defined in said upper half portion.

12. The method of claim of claim 10, wherein:
    said mixing blade has an upper half portion and a lower half portion,
    at least a first pair of said plurality of outlet orifices is defined in said upper half portion, and
    at least a second pair of said plurality of outlet orifices is defined in said lower half portion.

13. The method of claim of claim 12, wherein:
    each of said first pair of said plurality of outlet orifices is vertically spaced apart from each other, and
    each of said second pair of said plurality of outlet orifices is vertically spaced apart from each.

14. The method of claim 10, wherein:
    said mixing blade includes a shaft having a distal end, and
    at least one of said plurality of outlet orifices is spaced apart from said distal end of said shaft.

15. The method of claim 10, wherein:
    said plurality of outlet orifices includes at least seven outlet orifices, and
    each outlet orifice of said at least seven outlet orifices is vertically spaced apart from each other along the length of said shaft.

16. The method of claim 10, wherein the rotating step includes the steps of (i) moving a handle so as to rotate a plurality of mixing gears of a gear assembly, and (ii) rotating said mixing blade in response to rotation of said plurality of mixing gears of said gear assembly, further comprising the step of:
    advancing said liquid bone cement component through said gear assembly to said inlet orifice of said mixing blade.

17. The method of claim 16, wherein the step of advancing said liquid bone cement component through said gear assembly to said inlet orifice of said mixing blade includes the step of advancing said liquid bone cement component through a channel defined in at least one of said plurality of mixing gears of said gear assembly.

18. A bone cement mixing apparatus, comprising:
    a container defining a mixing chamber; and
    a mixing blade positioned within said mixing chamber, said mixing blade defining (i) an inlet orifice, (ii) a plurality of outlet orifices, and (iii) a passageway which places said inlet orifice in fluid communication with each of said plurality of outlet orifices.

19. The bone cement mixing apparatus of claim 18, wherein:
   said mixing blade has an upper half portion and a lower half portion, and
   at least one of said plurality of outlet orifices is defined in said upper half portion.

20. The bone cement mixing apparatus of claim 18, wherein:
   said mixing blade has an upper half portion and a lower half portion,
   at least two of said plurality of outlet orifices are defined in said upper half portion and vertically spaced apart from each other, and
   at least another two of said plurality of outlet orifices are defined in said lower half portion and vertically spaced apart from each other.

21. The bone cement mixing apparatus of claim 18, wherein:
   said mixing blade includes a shaft having a distal end, and
   at least one of said plurality of outlet orifices is spaced apart from said distal end of said shaft.

22. The bone cement mixing apparatus of claim 18, wherein:
   said plurality of outlet orifices includes at least seven outlet orifices, and
   each outlet orifice of said at least seven outlet orifices is vertically spaced apart from each other.

23. The bone cement mixing apparatus of claim 18, further comprising:
   a gear assembly having an output gear mechanically coupled to said mixing blade; and
   a fluid tube which extends through said gear assembly, said fluid tube being in fluid communication with said inlet orifice of said mixing blade.

24. The bone cement mixing apparatus of claim 23, further comprising a handle mechanically coupled to an input gear of said gear assembly, wherein:
   said handle has a fluid delivery port defined therein, and
   said fluid tube is in fluid communication with said fluid delivery port.

25. The bone cement mixing apparatus of claim 18, further comprising:
   a gear assembly having a plurality of mixing gears which cooperate with each other to transmit force to said mixing blade; and
   a fluid tube which (i) is in fluid communication with said inlet orifice of said mixing blade, and (ii) extends through at least one of said plurality of mixing gears.

* * * * *